US011365211B2

(12) United States Patent
Zhang et al.

(10) Patent No.: US 11,365,211 B2
(45) Date of Patent: Jun. 21, 2022

(54) STEREOSELECTIVE SYNTHESIS AND PROCESS FOR THE MANUFACTURING OF 2'-DEOXYNUCLEOSIDES

(71) Applicants: The USA, as represented by the Secretary, Department of Health and Human Services, Bethesda, MD (US); Alchem Laboratories Corporation, Alachua, FL (US)

(72) Inventors: Lianhao Zhang, Alachua, FL (US); Baburao Vishnuvajjala, Rockville, MD (US); Joel Morris, Rockville, MD (US); Robert Bahde, Gaithersburg, MD (US); Sergiy M. Denysenko, Gainesville, FL (US); Omar Diego Lopez, Walkersville, MD (US); Donn Gregory Wishka, Middletown, MD (US)

(73) Assignee: The United States of America, as represented by the Secretary, Department of Health and Human Services, Bethesda, MD (US)

(*) Notice: Subject to any disclaimer, the term of this patent is extended or adjusted under 35 U.S.C. 154(b) by 0 days.

(21) Appl. No.: 16/966,398

(22) PCT Filed: Jan. 30, 2019

(86) PCT No.: PCT/US2019/015763
§ 371 (c)(1),
(2) Date: Jul. 30, 2020

(87) PCT Pub. No.: WO2019/152459
PCT Pub. Date: Aug. 8, 2019

(65) Prior Publication Data
US 2020/0361977 A1 Nov. 19, 2020

Related U.S. Application Data

(60) Provisional application No. 62/624,967, filed on Feb. 1, 2018.

(51) Int. Cl.
*C07H 1/00* (2006.01)
*C07H 23/00* (2006.01)
(52) U.S. Cl.
CPC .............. *C07H 1/00* (2013.01); *C07H 23/00* (2013.01)
(58) Field of Classification Search
CPC ........... C07H 1/00; C07H 19/06; C07H 23/00
See application file for complete search history.

(56) References Cited

FOREIGN PATENT DOCUMENTS

WO    WO 2013/019794 A1    2/2013

OTHER PUBLICATIONS

Sugimara et al., J. Org. Chem., 1994, 59, p. 7653-7660. (Year: 1994).*
Haraguchi et al., J. Org. Chem., 2002, 67, p. 5919-5927. (Year: 2002).*
Haraguchi et al., "Electrophilic Addition to 4-Thio Furanoid Glycal: a Highly Stereoselective Entry to 2'-Deoxy-4'-Thio Pyrimidine Nucleosides," *Tetrahedron Letters* 39(22): 3713-3716 (May 28, 1998).
International Search Report and Written Opinion, dated Mar. 25, 2019, issued in corresponding International Application No. PCT/US2019/015763.
Mata et al., "Stereoselective N-Glycosylation of 2-Deoxythioribosides for Fluorescent Nucleoside Synthesis," *The Journal of Organic Chemistry* 77(20): 9006-9017 (Sep. 13, 2012).
"Preclinical Development of T-dCyd," Drug Synthesis and Chemistry Branch (DSCB), Jun. 17, 2015, retrieved from https://dtp.cancer.gov/organization/dscb/smchemistry/-tdcyd.htm on Sep. 15, 2017.
Sugimura et al., "Stereoselective Synthesis of 2'-Deoxy-β-threo-pentofuranosyl Nucleosides by the NBS-Promoted Coupling Reaction of Thioglycosides with Silylated Heterocyclic Bases," *The Journal of Organic Chemistry* 59(25): 7653-7560 (Dec. 1, 1994).
Tiwari et al., "Synthesis and Anti-cancer Activity of Some Novel 5-Azacytosine Nucleosides," *Nucleosides, Nucleotides & Nucleic Acids*, 22(12):2161-2170 (2003).
Toyohara et al., "Alkyl-fluorinated thymidine derivatives for imaging cell proliferation: I. The in vitro evaluation of some alkyl-fluorinated thymidine derivatives," *Nuclear Medicine and Biology* 33(6):751-764 (Aug. 1, 2006).
Wilson et al., "Nitrogen Glycosylation Reactions Involving Pyrimidine and Purine Nucleoside Bases with Furanoside Sugars," *Nitrogen Glycosylation Reactions Involving Pyrimidine and Purine Nucleoside Bases*, 1465-1479 (Dec. 1995).

* cited by examiner

*Primary Examiner* — Jonathan S Lau
(74) *Attorney, Agent, or Firm* — Klarquist Sparkman, LLP

(57) ABSTRACT

Methods for stereoselective synthesis and manufacturing of 2'-deoxynucleosides, such as 2'-ribonucleosides, are disclosed. In some embodiments, the 2'-deoxynucleoside is a β-anomer of a 2'-deoxynucleoside having a 3' α hydroxyl, 4' β hydroxymethyl configuration. Nonlimiting examples of compounds prepared by the disclosed methods include 4'-thio-2'-deoxycytidine (T-dCyd) and 5-aza-4'-thio-2'-deoxycytidine (5-aza-T-dCyd; aza-T-dCyd; aza-T-dC).

13 Claims, 7 Drawing Sheets

Scheme 3.

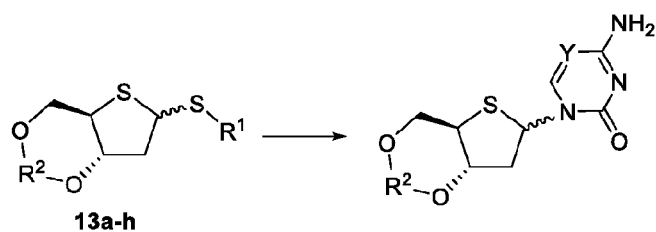

| Ex. | Coupling Thiosugar | R¹ | R² | Y | Observed β/α Ratio | Isolated Yield β |
|---|---|---|---|---|---|---|
| 1 | 13a | 4-OC₈H₁₇-benzyl | -(iPr)₂SiOSi(iPr)₂- | N | 4:1 | 44% |
| 2 | 13a | 4-OC₈H₁₇-benzyl | -(iPr)₂SiOSi(iPr)₂- | CH | 5.2:1 | 54% |
| 3 | 13b | benzyl | -(iPr)₂SiOSi(iPr)₂- | N | 4:1 | 47% |
| 4 | 13c | phenyl | -(iPr)₂SiOSi(iPr)₂- | N | 2:1 | 26% |
| 5 | 13e | 4-OCH₃-phenyl | -(iPr)₂SiOSi(iPr)₂- | N | 4:1 | ND* |
| 6 | 13f | 4-F-phenyl | -(iPr)₂SiOSi(iPr)₂- | N | 2:1 | ND |
| 7 | 13d | 4-OCH₃-benzyl | -(iPr)₂SiOSi(iPr)₂- | N | 4:1 | 46% |
| 8 | 13g | 4-OC₈H₁₇-benzyl | -(CH₃)₂SiOSi(CH₃)₂- | N | 2.5:1 | ND |
| 9 | 13h | 4-OC₈H₁₇-benzyl | -(Ph)₂SiOSi(Ph)₂- | N | 4:1 | ND |
| 10 | 13a | 4-OC₈H₁₇-benzyl | -(iPr)₂SiOSi(iPr)₂- | CF | 4:1 | ND |

*ND = not determined

FIG. 6

STEREOSELECTIVE SYNTHESIS AND PROCESS FOR THE MANUFACTURING OF 2'-DEOXYNUCLEOSIDES

CROSS REFERENCE TO RELATED APPLICATIONS

This is the U.S. National Stage of International Application No. PCT/US2019/015763, filed Jan. 30, 2019, which was published in English under PCT Article 21(2), which in turn claims the benefit of the earlier filing date of U.S. Provisional Application No. 62/624,967, filed Feb. 1, 2018, each of which is incorporated by reference in its entirety herein.

FIELD

Embodiments of a method for stereoselective synthesis of 2'-deoxynucleosides are disclosed.

BACKGROUND

The development of a stereoselective synthesis of 2'-deoxy-β-pentofuranosyl nucleosides is challenging due to the empirical nature of the exercise where the application of known chemistry from very closely related systems is often met with limited success. The stereoselective synthesis of 2'-deoxy-β-pentothiofuranosyl nucleosides is complicated by the lack of chemical equivalence between pentofuranosyl thioglycosides and pentothiofuranosyl thioglycosides. Even greater challenges arise when the pentothiofuranosyl thioglycoside has a 3' α hydroxyl, 4' β hydroxymethyl to give the erythro or D configuration.

Sugimura discloses a method for the stereoselective synthesis of 2'-deoxy-β-threo-pentofuranosyl nucleosides by N-bromosuccinimide (NBS)-promoted coupling reaction of thioglycosides with silylated heterocyclic bases (*J. Org. Chem.* 1994, 59:7653-7660). Sugimura reports that the β anomer is preferentially synthesized when threo-pentofurano-1-thioglycosides 5a-f are coupled with thymine in the presence of NBS (DCM) to give 2'-deoxy-β-threo-pentofuranosyl nucleosides 6a-f:

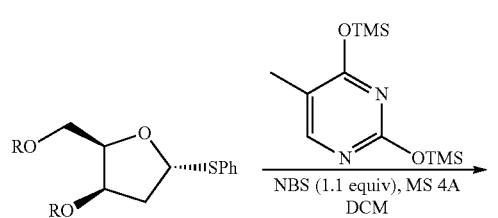

5a, R = Ac
5b, R = Bz
5c, R = Bn
5d, R = t-BuMe$_2$Si
5e, R,R = >CMe$_2$
5f, R,R = >CHPh (1)

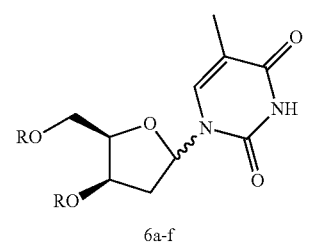

6a-f

Sugimura hypothesizes that, regardless of the initial orientation of the —SPh group, NBS is sterically favored to form intermediate (D) with the starting compound, which then reacts with persilylated thymine to give the βnucleoside (page 7655).

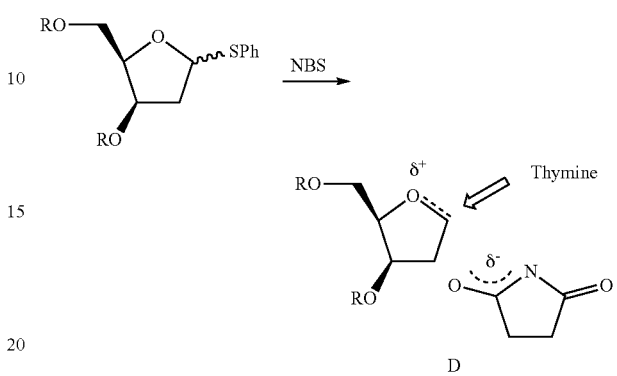

D

Sugimura proposes that the high diastereoselectivity observed during the reaction of the ketal or acetal protected thioglycoside is due to the fixed conformation with steric repulsion leading to formation of the intermediate D and subsequent reaction with the silylated thymine derivative to give the β-nucleoside (page 7655). Sugimura further discloses that a bicyclic ketal protected threo-thioglycoside enhances the conformational bias of intermediate D to produce very high levels of diastereoselectivity in the base addition step to provide the desired β anomer (page 7654).

Other investigators have determined that 2'-deoxyribosides having a 3' α hydroxyl, 4' β hydroxymethyl (erythro) configuration couple with silylated bases without stereoselectivity. For example, Wilson (*Nitrogen Glycosylation Reactions Involving Pyrimidine and Purine Nucleoside Bases* 1995, 1465-1479) discovered that use of a 1-phenylthio group and NBS, as suggested by Sugimura, did not provide stereoselectivity in a 2'-deoxyriboside having a 3' α, 4' β configuration and resulted in an α:β ratio of 2:1 (pp. 1475-1476). Wilson attributes the lack of stereoselectivity to formation of an oxonium intermediate, thereby losing stereospecificity of the α-phenylthio group (page 1476).

SUMMARY

Methods for stereoselective synthesis and manufacturing of 2'-deoxynucleosides, such as 2'-ribonucleosides, are disclosed. In some embodiments, the 2'-deoxyribonucleoside is a β-anomer of a 2'-deoxynucleoside having a 3' α hydroxyl and 4' β hydroxymethyl corresponding to the erythro or D configuration.

In certain embodiments, a method for stereoselective synthesis of a β-anomer of a nucleoside includes providing a compound having a structure and stereochemistry according to Formula I

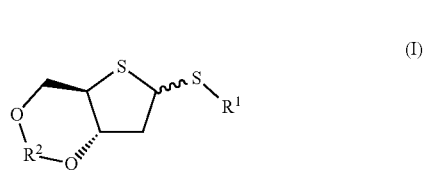

(I)

wherein R$^1$ is optionally substituted —(CH$_2$)$_n$-aryl, or —(CH$_2$)$_n$-alkyl where n is 0, 1, or 2; and R$^2$ is a protecting group having a formula —Si($R^a$)($R^b$)—O—Si($R^a$)($R^b$)— where each $R^a$ and $R^b$ independently is alkyl, cycloalkyl, or aryl. The method further includes combining the compound according to Formula I with a halogenating agent, such as N-bromosuccinimide and a silylated pyrimidine under reaction conditions effective to produce a mixture of α- and β-anomers of a protected pyrimidine-based nucleoside, separating the β-anomer from the α-anomer of the protected nucleoside, and removing the protecting group from the β-anomer of the protected pyrimidine-based nucleoside to provide a β-anomer of a pyrimidine-based nucleoside. In any or all of the foregoing embodiments, the mixture of α- and β-anomers produced by the method may have a β/α mass ratio of at least 2:1.

In the foregoing embodiments, $R^2$ is a protecting group having a formula —Si($R^a$)($R^b$)—O—Si($R^a$)($R^b$)—. In some embodiments, $R^a$ and $R^b$ independently are $C_1$-$C_4$ alkyl, cycloalkyl, or phenyl. $R^a$ and $R^b$ may be the same or different. In certain examples, $R^2$ is —Si(CH($CH_3$)$_2$)$_2$—O—Si(CH($CH_3$)$_2$)$_2$—, —Si($CH_3$)$_2$—O—Si($CH_3$)$_2$—, or —Si($C_6H_5$)$_2$—O—Si($C_6H_5$)$_2$—.

In any or all of the above embodiments, $R^1$ may be aryl or —(CH$_2$)$_n$-aryl, where the aryl is optionally substituted with alkyl, alkoxy, or halo, and n=0 or 1. In some examples, $R^1$ is:

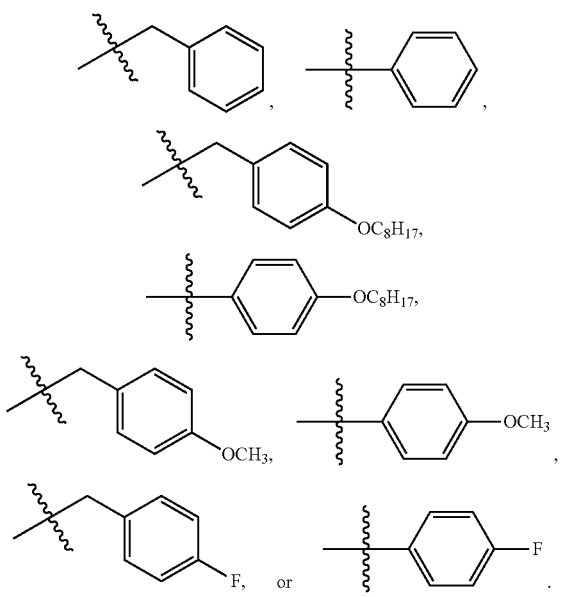

In any or all of the above embodiments, the β-anomer of the pyrimidine-based nucleoside has a general structure:

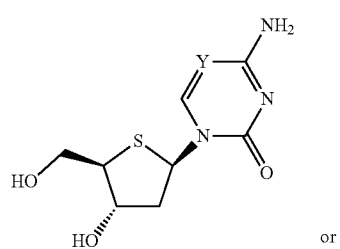

or

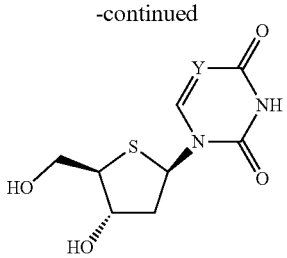

wherein Y is N, C(H), C(CH$_3$) or C(X) where X is halo. In certain examples, the β-anomer of the pyrimidine-based nucleoside is

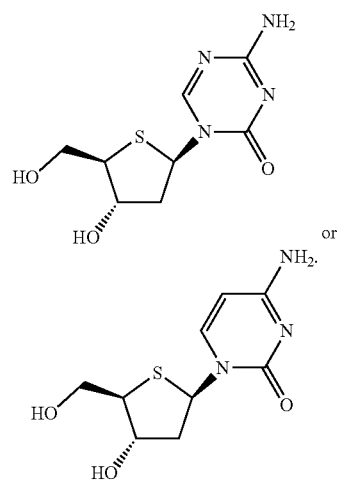

The foregoing and other objects, features, and advantages of the invention will become more apparent from the following detailed description, which proceeds with reference to the accompanying figures.

BRIEF DESCRIPTION OF THE DRAWINGS

FIG. 6 provides data for several 2'-deoxynucleosides synthesized according to the methods disclosed herein.

DETAILED DESCRIPTION

Figure 1:
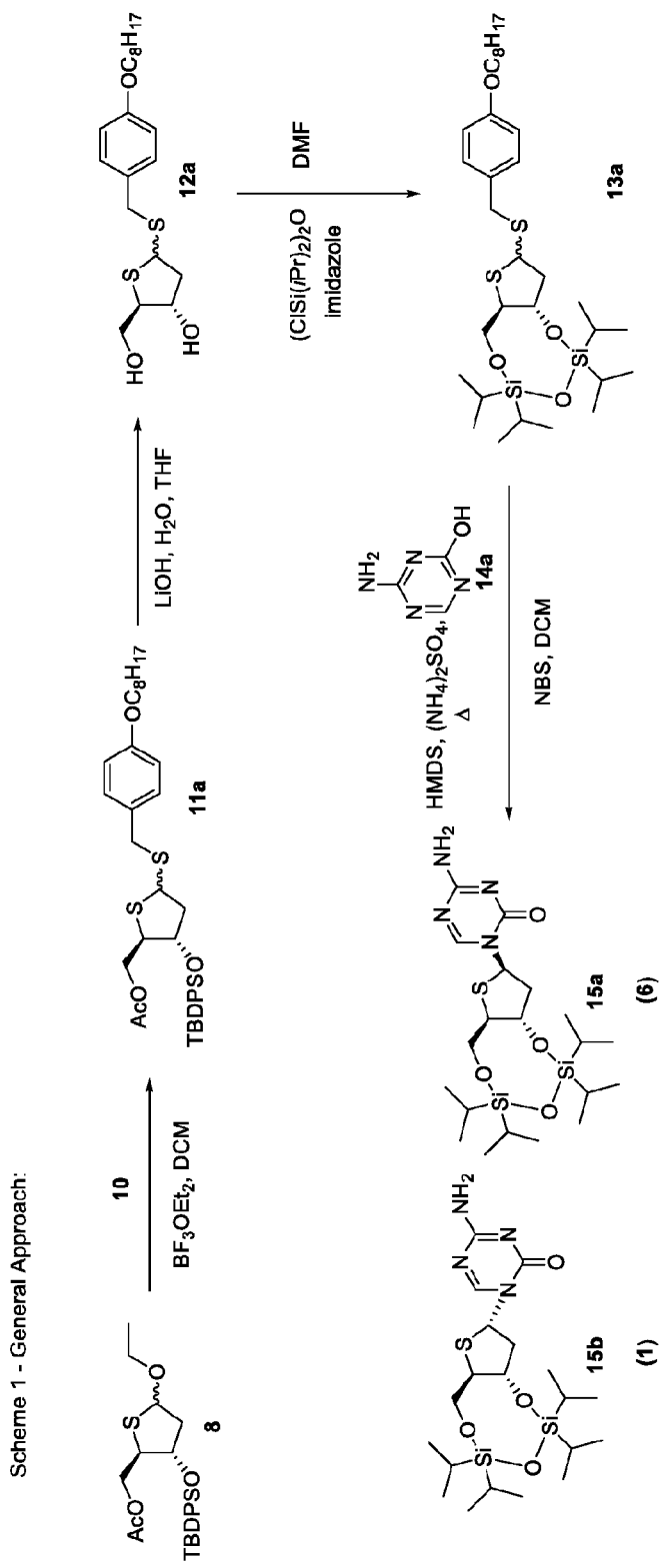
FIG. 1 is an exemplary synthetic scheme for making a 2'-deoxynucleoside.

Embodiments of a stereoselective synthesis and process for the manufacturing of 2'-deoxynucleosides, such as 2'-deoxyribonucleosides are disclosed. In some embodiments, the process provides a β-anomer to α-anomer mass ratio of at least 2:1. Advantageously, the anomers can be separated without the use of expensive and difficult processes such as supercritical fluid chromatography. Embodiments of the disclosed process are useful for synthesizing multi-gram quantities of the 2'-deoxyribonucleosides. In some embodiments, the 2'-deoxyribonucleoside is a 2'-deoxy-β-erythro-pentothiofuranosyl nucleoside. Some embodiments of the disclosed 2'-deoxy-β-erythro-pentothiofuranosyl nucleosides are useful as anti-cancer agents. For example, the β-anomers of 4'-thio-2'-deoxycytidine (T-dCyd; 4-amino-1-((2R,4S,5R)-4-hydroxy-5-(hydroxymethyl)tetrahydrothiophen-2-yl)pyrimidine-2(1H)-one) and 5-aza-4'-thio-2'-deoxycytidine (5-aza-T-dCyd; aza-T-dCyd; aza-T-dC; 4-amino-1-((2R,4S,5R)-4-hydroxy-5-(hydroxymethyl)tetrahydrothiophen-2-yl)-1,3,5-trazin-2(1H)-one) are nucleosides shown to deplete DNA methyltransferase I (DNMT1), thereby inhibiting tumor growth (Tholtassery et al., *Cancer Chemother Pharmacol.* 2014, 74(2):291-302).

I. DEFINITIONS AND ABBREVIATIONS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximates unless the word "about" is recited.

Although there are alternatives for various components, parameters, operating conditions, etc. set forth herein, that does not mean that those alternatives are necessarily equivalent and/or perform equally well. Nor does it mean that the alternatives are listed in a preferred order unless stated otherwise.

Definitions of common terms in chemistry may be found in Richard J. Lewis, Sr. (ed.), *Hawley's Condensed Chemical Dictionary*, published by John Wiley & Sons, Inc., 1997 (ISBN 0-471-29205-2). In order to facilitate review of the various embodiments of the disclosure, the following explanations of specific terms are provided:

Alkyl: A hydrocarbon group having a saturated carbon chain. The chain may be cyclic, branched or unbranched. Examples, without limitation, of alkyl groups include methyl, ethyl, propyl, butyl, pentyl, hexyl, heptyl, octyl, nonyl and decyl.

Alkoxy: A radical (or substituent) having the structure —OR, where R is a substituted or unsubstituted alkyl. Methoxy (—OCH$_3$) is an exemplary alkoxy group. In a substituted alkoxy, R is alkyl substituted with a non-interfering substituent.

Anomer: An epimer (an isomer having a different configuration at just one chiral carbon) occurring in cyclic saccharides.

Aryl: A monovalent aromatic carbocyclic group of, unless specified otherwise, from 6 to 15 carbon atoms having a single ring (e.g., phenyl) or multiple condensed rings in which at least one ring is aromatic (e.g., quinoline, indole, benzodioxole, and the like), provided that the point of attachment is through an atom of an aromatic portion of the aryl group and the aromatic portion at the point of attachment contains only carbons in the aromatic ring. If any aromatic ring portion contains a heteroatom, the group is a heteroaryl and not an aryl. Aryl groups are monocyclic, bicyclic, tricyclic or tetracyclic.

Cycloalkyl: A saturated monovalent cyclic hydrocarbon radical of three to seven ring carbons, e.g., cyclopentyl, cyclohexyl, cycloheptyl and the like.

Diastereomers: Optically active isomers containing two or more asymmetric carbons with differing configurations at one or more of the stereocenters and are not mirror images of each other:

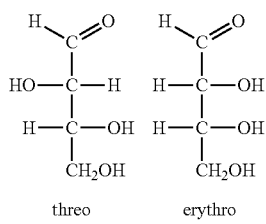

threo    erythro

Nucleoside: A compound containing a purine or pyrimidine base linked to either d-ribose, forming a riboside, or d-deoxyribose, forming a deoxyriboside. Nucleosides are nucleotides minus the phosphorus group.

Protecting or Protective Group: To synthesize organic compounds, often some specific functional group cannot survive the required reagents or chemical environments. These groups must be protected. A protecting group, or protective group, is introduced into a molecule by chemical modification of a functional group in order to obtain chemoselectivity in a subsequent chemical reaction. Various exemplary protecting or protective groups are disclosed in Greene's Protective Groups in Organic Synthesis, by Peter G. M. Wuts and Theodora W. Greene (Oct. 30, 2006), which is incorporated herein by reference. A compound that includes a protecting group is said to be protected.

Purine: A heterocyclic aromatic organic compound including a pyrimidine ring fused to an imidazole ring. Naturally occurring purines found in nucleosides include adenine and guanine.

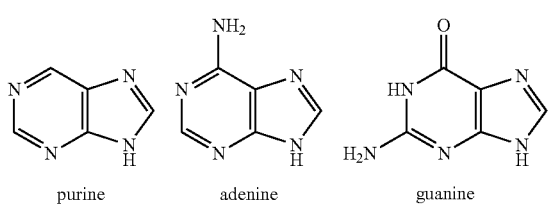

purine     adenine     guanine

Pyrimidine: A heterocyclic aromatic organic compound having the general formula $C_4H_4N_2$ with nitrogen atoms at positions 1 and 3 in the ring. Naturally occurring pyrimidines found in nucleosides include cytosine, thymine, and uracil.

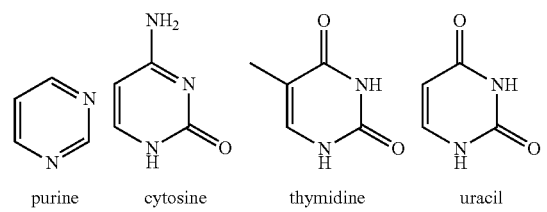

purine     cytosine     thymidine     uracil

Silyl: A functional group comprising a silicon atom bonded to different functional groups, and typically having a formula

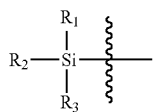

where $R_1$-$R_3$ independently are selected from various groups including, by way of example, hydrogen, aliphatic, substituted aliphatic, cyclic aliphatic, substituted cyclic aliphatic, aryl, substituted aryl, heteroaryl, and substituted heteroaryl. As used herein, the term "silylated" means that one or more amino or oxygen substituents on a pyrimidine, triazine, or purine is protected with a silyl group.

Stereochemistry: The three-dimensional spatial configuration of a molecule.

Stereoisomer: Isomers that have the same molecular formula and sequence of bonded atoms, but which differ only in the three-dimensional orientation of the atoms in space.

Stereoselective synthesis: A synthesis that preferentially forms one stereoisomer over another.

Substituent: An atom or group of atoms that replaces another atom in a molecule as the result of a reaction. The term "substituent" typically refers to an atom or group of atoms that replaces a hydrogen atom, or two hydrogen atoms if the substituent is attached via a double bond, on a parent hydrocarbon chain or ring. The term "substituent" may also cover groups of atoms having multiple points of attachment to the molecule, e.g., the substituent replaces two or more hydrogen atoms on a parent hydrocarbon chain or ring. In such instances, the substituent, unless otherwise specified, may be attached in any spatial orientation to the parent hydrocarbon chain or ring. Exemplary substituents include, for instance, alkyl, alkenyl, alkynyl, alkoxy, alkylamino, alkylthio, acyl, aldehyde, amido, amino, aminoalkyl, aryl, arylalkyl, arylamino, carbonate, carboxyl, cyano, cycloalkyl, dialkylamino, halo, haloaliphatic (e.g., haloalkyl), haloalkoxy, heteroaliphatic, heteroaryl, heterocycloaliphatic, hydroxyl, oxo, sulfonamide, sulfhydryl, thio, and thioalkoxy groups.

Substituted: A fundamental compound, such as an aryl or aliphatic compound, or a radical thereof, having coupled thereto one or more substituents, each substituent typically replacing a hydrogen atom on the fundamental compound. Solely by way of example and without limitation, a substituted aryl compound may have an aliphatic group coupled to the closed ring of the aryl base, such as with toluene. Again solely by way of example and without limitation, a long-chain hydrocarbon may have a hydroxyl group bonded thereto.

Triazine: A class of nitrogen-containing aromatic heterocycles. Unsubstituted triazines have a general formula $C_3H_3N_3$, and exist in three isomeric forms—1,2,3-triazine, 1,2,4-triazine, and 1,3,5-triazine. The most common isomer is 1,3,5-triazine.

II. STEREOSELECTIVE SYNTHESIS

Embodiments of a method of stereoselective synthesis of a β-anomer of a 2'-deoxyribonucleoside having a 3' α hydroxyl, 4' β hydroxymethyl (D, erythro) configuration are disclosed. The method includes providing a compound having a structure and stereochemistry according to Formula I

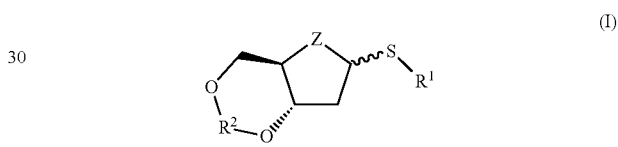

wherein Z is S or O; $R^1$ is optionally substituted aryl, —$(CH_2)_n$-aryl, -alkyl, or —$(CH_2)_n$-alkyl where n is 0 or 1; and $R^2$ is a protecting group having a formula —Si($R^a$)($R^b$)—O—Si($R^a$)($R^b$)— or —Si($R^a$)($R^b$)— where each $R^a$ and $R^b$ independently is alkyl, cycloalkyl, or aryl; combining the compound according to Formula I with N-bromosuccinimide and a silylated pyrimidine, triazine, or purine under reaction conditions effective to produce a mixture of α- and β-anomers of a protected pyrimidine-, triazine-, or purine-based nucleoside; separating the β-anomer from the α-anomer of the protected nucleoside; and removing the protecting group from the β-anomer of the protected nucleoside to provide a β-anomer of a pyrimidine-, triazine-, or purine-based nucleoside. In some embodiments, Z is S.

$R^1$ is optionally substituted —$(CH_2)_n$-aryl or —$(CH_2)_n$-alkyl where n is 0, 1, or 2. In some embodiments, $R^1$ is —$(CH_2)_n$-aryl where n is 0 or 1, and the aryl is optionally substituted with alkyl, alkoxy, or halo. The alkyl or alkoxy substituent may include from 1-10 carbon atoms. In certain embodiments, the aryl portion of $R^1$ is a phenyl group. Nonlimiting examples of $R^1$ groups include:

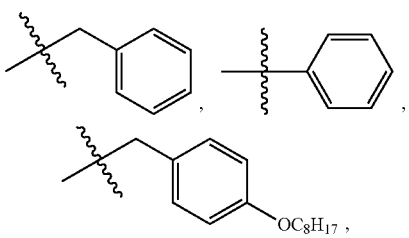

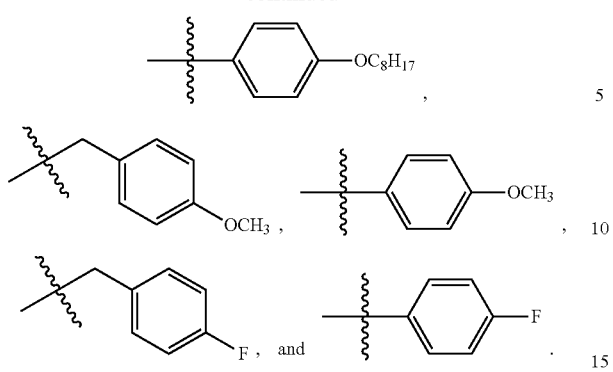

In any or all of the above embodiments, $R^2$ is a protecting group. In some embodiments, $R^2$ has a formula —Si($R^a$)($R^b$)—O—Si($R^a$)($R^b$)— or —Si($R^a$)($R^b$)— where each $R^a$ and $R^b$ independently is alkyl, cycloalkyl, or aryl. $R^2$ together with the atoms to which it is bound forms an 8- or 6-membered silylcycle. In some embodiments, $R^2$ together with the atoms to which it is bound forms an 8-membered silylcycle. In any of the foregoing embodiments, $R^a$ and $R^b$ independently may be $C_1$-$C_4$ alkyl (e.g., methyl, ethyl, isopropyl, t-butyl), $C_3$-$C_7$ cycloalkyl (e.g., cyclopentyl), or phenyl. In some embodiments, $R^a$ and $R^b$ are the same. Suitable $R^2$ groups include, but are not limited to, —Si(CH(CH$_3$)$_2$)$_2$—O—Si(CH(CH$_3$)$_2$)$_2$—, —Si(CH$_3$)$_2$—O—Si(CH$_3$)$_2$—, —Si(C$_6$H$_5$)$_2$—O—Si(C$_6$H$_5$)$_2$—, —Si(CH(CH$_3$)$_2$)$_2$—, —Si(CH$_3$)$_2$—, and —Si(C$_6$H$_5$)$_2$—. In some embodiments, the $R^2$ group is —Si(CH(CH$_3$)$_2$)$_2$—O—Si(CH(CH$_3$)$_2$)$_2$—, —Si(CH$_3$)$_2$—O—Si(CH$_3$)$_2$—, or —Si(C$_6$H$_5$)$_2$—O—Si(C$_6$H$_5$)$_2$—.

Exemplary compounds according to Formula I are shown in Table 1.

TABLE 1

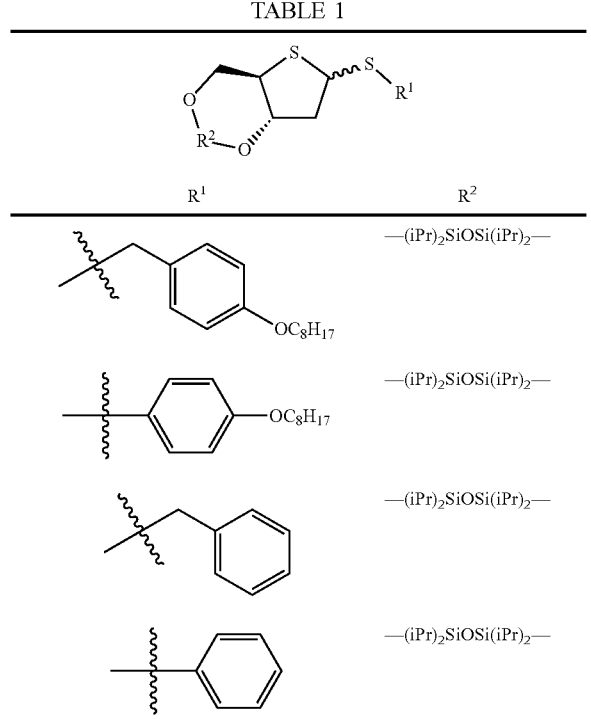

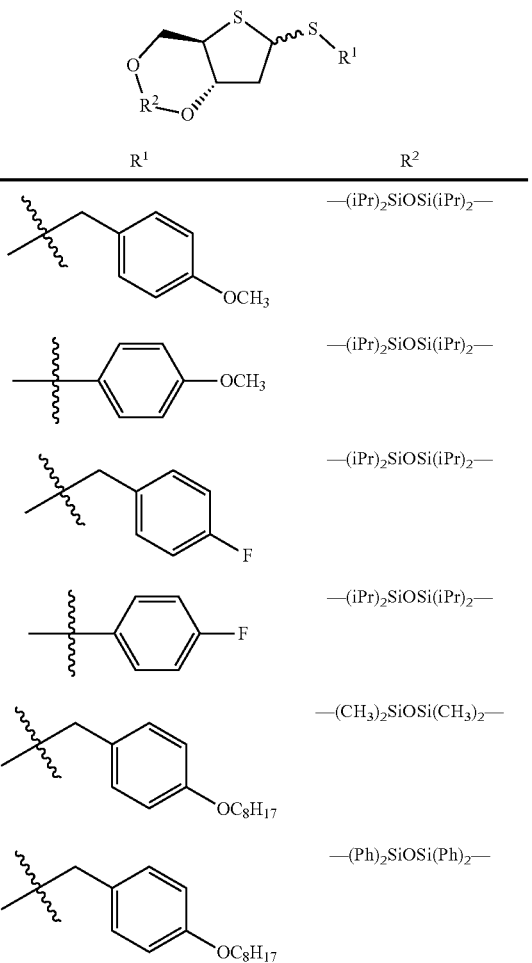

The compound according to Formula I is combined with a halogenating agent and a silylated pyrimidine, triazine, or purine under reaction conditions effective to produce a mixture of α- and β-anomers of a protected pyrimidine-based, triazine-based, or purine-based nucleoside. Suitable halogenating agents include, but are not limited to, brominating agents such as N-bromosuccinimide, pyrimidinium bromide, N-bromophthalimide, and the like. In some embodiments, the halogenating agent is N-bromosuccinimide.

In some embodiments, effective reaction conditions for producing a mixture of α- and β-anomers of a protected pyrimidine-based, triazine-based, or purine-based nucleoside include dissolving a silylated pryimidine, triazine, or purine in a suitable solvent, adding the compound according to Formula I, and mixing thoroughly. In some embodiments, the silylated pyrimidine, triazine, or purine is silylated in situ prior to addition of the compound according to Formula I. Advantageously, the compound according to Formula I is the limiting reactant, and a molar excess of the silylated pyrimidine, triazine, or purine is used. A molecular sieve (e.g., 4 Å), may be included. In some embodiments, the solvent is nonpolar or substantially nonpolar. Suitable solvents include, but are not limited to, dichloromethane, benzene, carbon tetrachloride, and the like. In certain embodiments, the solvent was dichloromethane. Mixing may be performed at a temperature below ambient temperature, such as a temperature from −10 to 10° C., for 10-60 minutes, such as from 10-30 minutes. In certain embodiments, mixing is performed at 0° C. After thorough mixing, NBS is added. The molar quantity of NBS is at least equivalent to the moles of the compound according to Formula I. In some embodiments, the molar quantity of NBS is from 1-1.5 equivalents relative to the compound according to Formula I. The reaction is allowed to proceed for a time effective to couple the silylated pyrimidine, triazine, or purine to the compound according to Formula I, producing a mixture of α- and β-anomers of a protected pyrimidine-based or purine-based nucleoside. The effective time may range from 30 minutes to several hours, such as from 30 minutes to 3 hours, 30 minutes to 2 hours, or 30-90 minutes. In some embodiments, the reaction time was one hour. The reaction may be performed at a temperature below ambient temperature, such as a temperature from −10 to 10° C. In certain examples, the temperature was 0° C. The reaction is quenched, e.g., by addition of sodium thiosulfate. In any or all of the above embodiments, an organic layer comprising the α- and β-anomers may be separated and extracted, e.g., with dichloromethane. The organic phase may be dried over magnesium sulfate to remove traces of water, filtered, and concentrated to provide a crude product including the α- and β-anomers. In any or all of the above embodiments, the crude product may have a β/α anomer mass ratio of at least 2:1. In some embodiments, the β/α anomer mass ratio is within a range of from 2:1 to 10:1, such as a β/α mass ratio of from 2:1 to 8:1, 2:1 to 7:1, 2:1 to 6:1, or 2:1 to 5:1.

In some embodiments, when the compound according to Formula I is combined with a silylated pyrimidine or triazine, the crude product has a structure according to Formula II or III where Y is N, C(H), C(CH$_3$) or C(X) where X is halo (F, Cl, Br, or I); Z and R$^2$ are as previously described. In certain embodiments, Z is S.

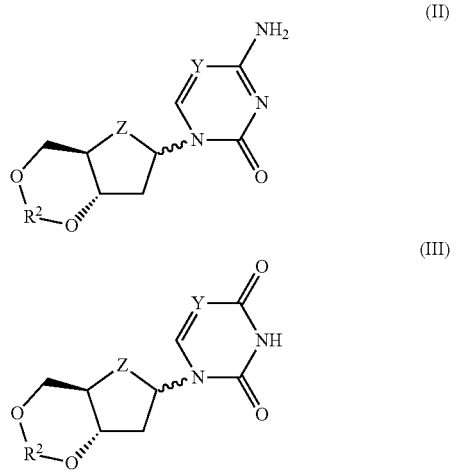

In some embodiments, when the compound according to Formula I is combined with a silylated purine, the crude product has a structure according to Formula IV or V where Z and R$^2$ are as previously described, R$^3$ is H or NH$_2$, and R$^4$ is H or NH$_2$. In certain embodiments, Z is S.

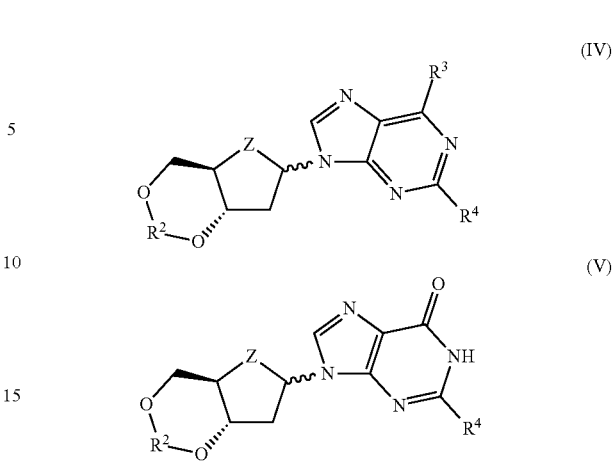

The α- and β-anomers of the protected nucleoside are separated to provide pure or substantially pure β-anomer. Advantageously, separation can be performed without supercritical fluid chromatography. Indeed, the anomers can be separated by column chromatography, such as silica gel chromatography. The eluent may be, for example, a gradient of ethyl acetate in dichloromethane, such as a 0-100% (v/v), 10-80% (v/v), 20-70% (v/v), or 30-50% (v/v) gradient of ethyl acetate in dichloromethane. In some embodiments, the β-anomer elutes first, followed by the α-anomer or a mixture of β-anomer and α-anomer. The β-anomer that elutes first may be pure β-anomer or substantially pure β-anomer, i.e., at least 90 wt % pure, at least 92 wt % pure, or at least 95 wt % pure.

Finally, the silyl protecting group (R$^2$) is removed from the β-anomer of the protected pyrimidine-based, triazine-based, or purine-based nucleoside to provide a β-anomer of a pyrimidine-based, triazine-based, or purine-based nucleoside. The silyl protecting group R$^2$ can be removed by any suitable method, such as by reaction with a fluoride-based compound. In some embodiments, the fluoride-based compound is ammonium fluoride or tetra-n-butylammonium fluoride. In certain embodiments, the fluoride-based compound is ammonium fluoride. In any or all of the foregoing embodiments, the deprotection reaction may be carried out by combining the protected pyrimidine-based, triazine based, or purine-based nucleoside in an anhydrous solvent (e.g., anhydrous C$_1$-C$_3$ alkanol, such as methanol) with the fluoride-based compound and reacting under conditions effective to remove the protecting group. Effective conditions may include a temperature within a range of from 30-90° C., such as from 40-80° C. or from 50-70° C., and/or a reaction time of from 30 minutes to 4 hours, such as a reaction time from 1-3 hours. Completion of the reaction may be assessed by conventional methods, such as by thin-layer chromatography. In some examples, deprotection was performed at 60° C. with a reaction time of 2-2.5 hours. In any or all of the above embodiments, the deprotected compound may be subsequently collected by filtration, washed, and concentrated to provide the β-anomer of the pyrimidine-based, triazine-based, or purine-based nucleoside. Further purification can be performed as desired, e.g., by flash chromatography. In some embodiments, the β-anomer has a structure and stereochemistry according to any one of Formulas VI-IX where Y, Z, R$^3$, and R$^4$ are as previously defined. In certain embodiments, Z is S.

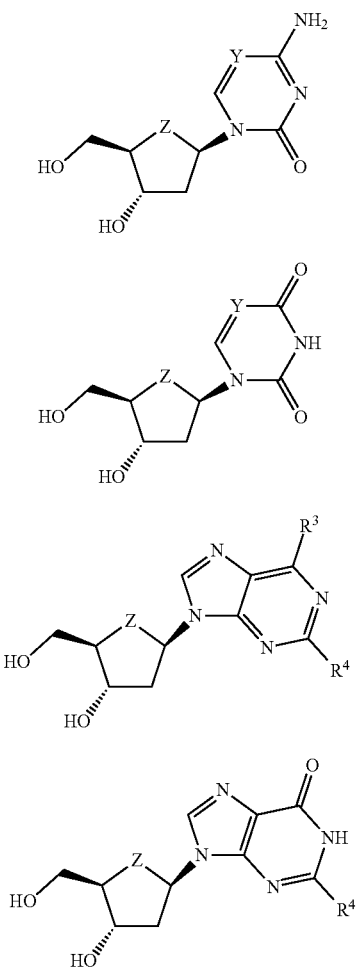

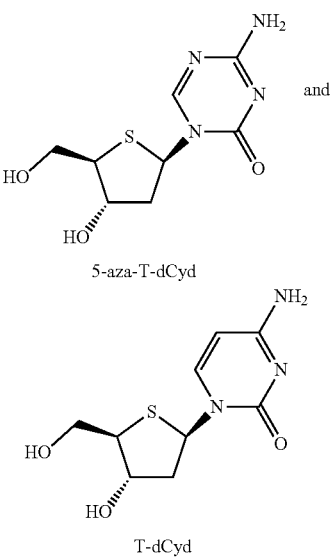

Two nonlimiting examples of β-anomers prepared by embodiments of the disclosed method are 5-aza-4'-thio-2'-deoxycytidine (5-aza-T-dCyd) and 4'-thio-2'-deoxycytidine (T-dCyd).

Embodiments of compounds according to Formula I are prepared by methods known to those of ordinary skill in the art of chemical synthesis. In brief, some embodiments of a compound according to Formula I are prepared by providing a diol compound having a structure and stereochemistry according to Formula X and
reacting the compound with a dihalo-disiloxane, e.g., a dichloro-disiloxane having a formula ClSi($R^a$)($R^b$)—O—Si($R^a$)($R^b$)Cl, under reaction conditions effective to produce the compound according to Formula I. $R^1$, $R^a$, and $R^b$ are as previously described. Effective reaction conditions may include combining the compound according to Formula X with imidazole and a solvent (e.g., N,N-dimethylformamide), cooling the solution to a temperature below ambient temperature (e.g., a temperature from −10 to 10° C.), and adding the dihalo-disiloxane. The reaction is allowed to proceed, without additional cooling, for a time effective to produce the compound according to Formula I. In some embodiments, the effective time is from to one to several hours, such as from 1-24 hours, from 4-20 hours, or from 8-20 hours.

Schemes 1-3 (FIGS. 1-3) show one exemplary synthetic route for making a compound according to Formula I where R' is —$CH_2$—$C_6H_4$—$OC_8H_{17}$. Scheme 2 (FIG. 2) illustrates an exemplary method for making the thiosugar. A reaction between 4,4-diethoxybut-1-ene (1) and (Z)-but-2-ene-1,4-diyl diacetate forms (E)-5,5-diethoxypent-2-en-1-yl acetate (2). Compound 2 is reacted with potassium carbonate to form (E)-5,5-diethoxypent-2-en-1-ol (3). Compound 3 is subsequently converted to the epoxide ((2S,3S)-3-(2,2-diethoxyethyl)oxiran-2-yl)methanol (4). Treatment of 4 with carbon disulfide, tetrahydrofuran, and sodium bis(trimethylsilyl)amide provides (R)-4-((S)-3,3-diethoxy-1-hydroxypropyl)-1,3-oxathiolane-2-thione (5) and (R)-4-((S)-3,3-diethoxy-1-((trimethylsilyl)oxy)propyl)-1,3-oxathiolane-2-thione. The (R)-4-((S)-3,3-diethoxy-1-((trimethylsilyl)oxy)propyl)-1,3-oxathiolane-2-thione is desilylated to provide additional compound 5. Compound 5 is treated with imidazole and tert-butylchlorodiphenylsilane (TBDPS) to form (R)-4-((S)-1-((tert-butyldiphenylsilyl)oxy)-3,3-diethoxypropyl)-1,3-oxathiolane-2-thione (6). Compound 6 is reacted with potassium carbonate to form tert-butyl((S)-3,3-diethoxy-1-((S)-thiiran-2-yl)propoxy)diphenylsilane (7). Compound 7 is converted to ((2R,3S)-3-((tert-butyldiphenylsilyl)oxy)-5-ethoxytetrahydrothiophen-2-yl)methyl acetate (8) by reaction in acetic acid, acetic anhydride, and potassium acetate.

Figure 3:
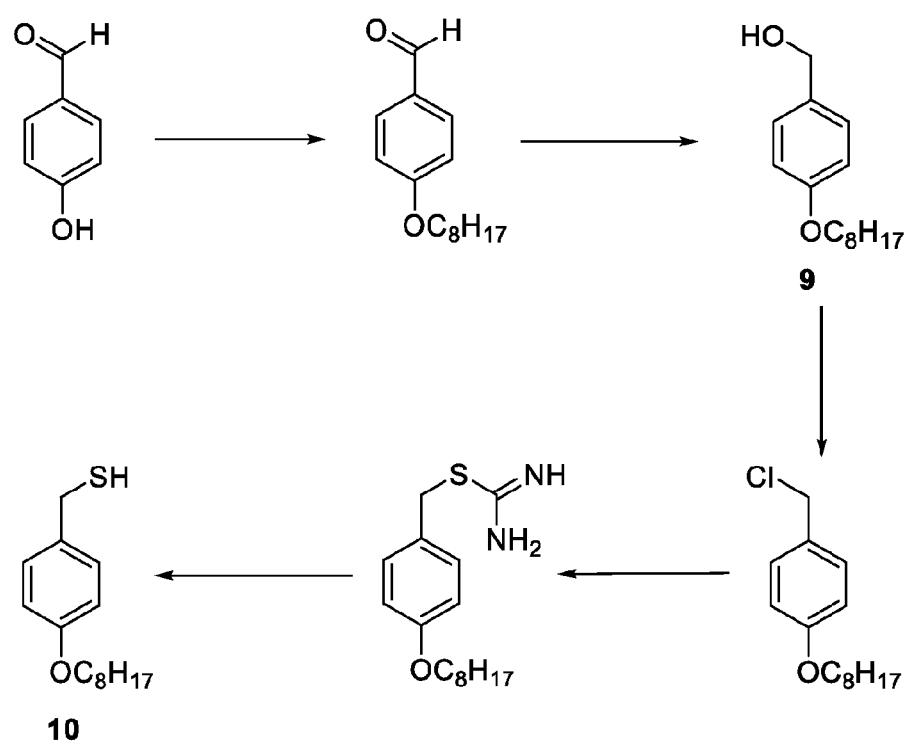
FIG. 3 is an exemplary synthetic scheme for making 4-octyloxyphenylmethane thiol.

One exemplary route for synthesizing 4-octyloxyphenylmethane thiol is shown in FIG. 3. A mixture of 4-hydroxybenzaldehyde, 1-bromooctane, and potassium carbonate in acetonitrile is refluxed and the resulting aldehyde is reduced to form 4-octyloxyphenylmethanol (9). Compound 9 is reacted with HCl and acetonitrile to form the methyl chloride, followed by reaction with thiourea and acetonitrile. Subsequent refluxing with sodium hydroxide followed by addition to HCl provides 4-octyloxyphenylmethanethiol (10).

Compounds 8 and 10 are combined in dichloromethane and boron trifluoride diethyl etherate is added dropwise, followed by addition of triethylamine to form ((2R,3S)-3-((tert-butyldiphenylsilyl)oxy)-5-((4-octyloxybenzyl)thio)-tetrahydrothiophen-2-yl)methyl acetate (11a) (Scheme 1, FIG. 1). Compound 11a is added to tetrahydrofuran, mixed with a solution of lithium hydroxide and refluxed to remove the acetyl and silylated groups, thereby forming (4S,5R)-4-hydroxy-5-hydroxymethyl-2-((4-(octyloxy)benzyl)thio)-tetrahydrothiophene (12a). The diol is protected by reaction of compound 12a with 1,3-dichloro-1,1,3,3-tetraisopropyldisiloxane in a solution containing imidazole and N,N-dimethylformamide to provide 6aR,9aS)-2,2,4,4-tetraisopropyl-8-((4-(octyloxy)benzyl)thio)tetrahydro-6H-thieno[3,2-f][1,3,5,2,4]trioxadisilocine (13a), a compound according to Formula I. Syntheses of other compounds according to Formula I are detailed below in the Examples.

Without wishing to be bound by a particular theory of operation, the 8-membered silylcycle formed when the disiloxane reacts with the 3' α hydroxyl and 4'β hydroxymethyl groups constrains the pentothiofuranosyl ring in a planar configuration. A tight ion pair is formed with NBS, wherein the succinimidyl group apparently associates primarily with the α-face of the compound according to Formula I. Subsequent coupling to the silylated pyrimidine, triazine, or purine occurs primarily at the β-face of the compound leading to stereoselectivity with preferential formation of the β-anomer. This finding was very surprising since preferential association of the succinimidyl group with the α-face of the planar pentothiofuranosyl ring was not predictable and was unexpected in the absence of steric repulsion that occurs with a β, β configuration.

As discussed in the Background, Sugimura (*J. Org. Chem.* 1994, 59:7653-7660) discloses stereoselective synthesis of 2'-deoxy-β-threo-pentofuranosyl nucleosides by NB S-promoted coupling reaction of thioglycosides with silylated heterocyclic bases. However, Sugimura does not teach or suggest that the method will be similarly stereoselective with a thiofuranose, let alone an erythro-thiofuranose. For example, base couplings of thio sugars to produce nucleosides generally proceed with α-selectivity, greatly reducing the synthetic efficiency when a β-anomer is desired. Moreover, other investigators, such as Wilson (*Nitrogen Glycosylation Reactions Involving Pyrimidine and Purine Nucleoside Bases* 1995, 1465-1479), determined that 2'-deoxyribosides having a 3' α, 4' β configuration couple with silylated bases in the presence of NBS without stereoselectivity. This result is not surprising. It is impossible for the erythro-thiofuranose to adopt the conformation of Sugimura's intermediate, and the α, β configuration of the furanose cannot provide the same steric repulsion as Sugimura's β, β configuration wherein the ring substituents are in close proximity to one another.

Nonetheless, the inventors prepared erythro-thio-furanothioglycosides A and B, and subjected the compounds to the reaction conditions described by Sugimura.

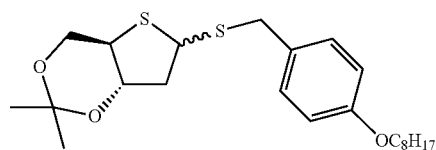

A

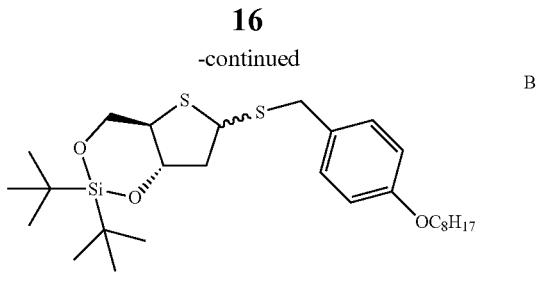

B

Under Sugimura s reaction conditions, starting material was consumed, no base addition product was isolated, and the isolated material appeared to be the degraded erythro-thiofuranothioglycoside. None of the desired product was obtained.

Figure 4:
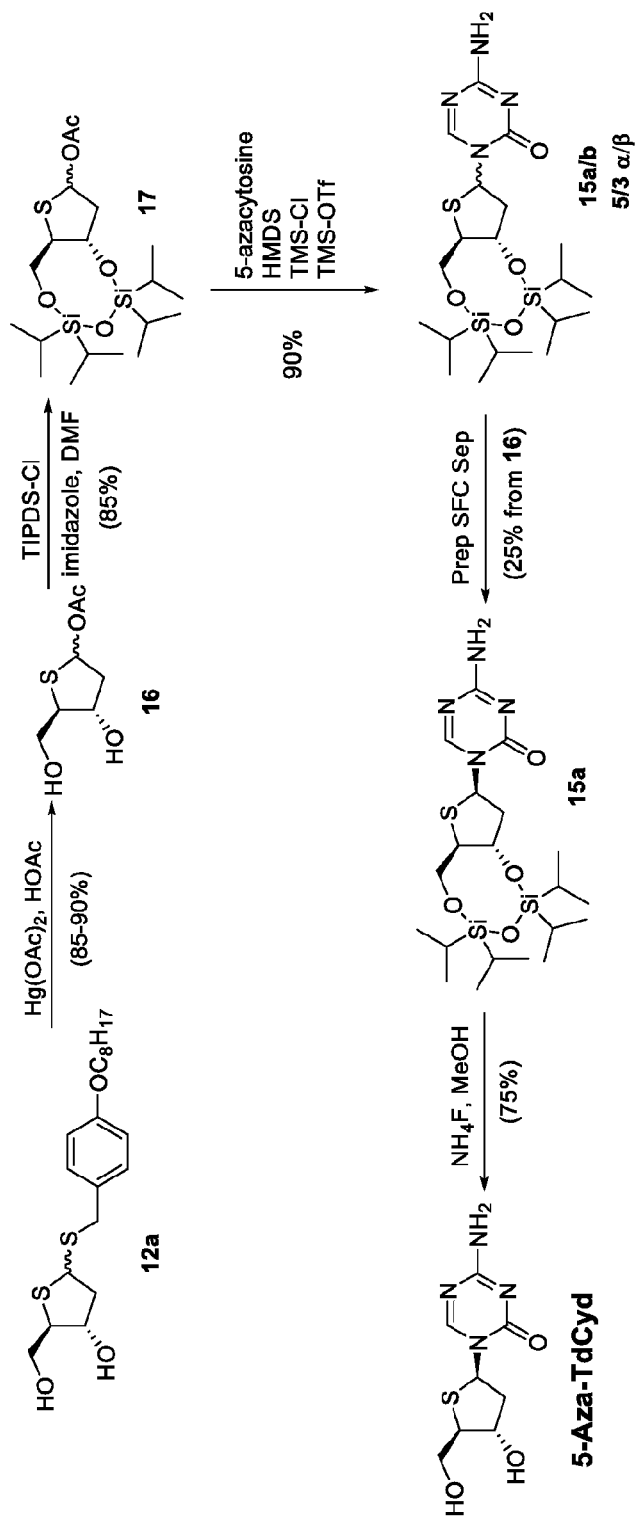
FIG. 4 is a prior art synthetic scheme showing a route for making 5-aza-4'-thio-2'-deoxycytidine (5-aza-T-dCyd).
Figure 5:
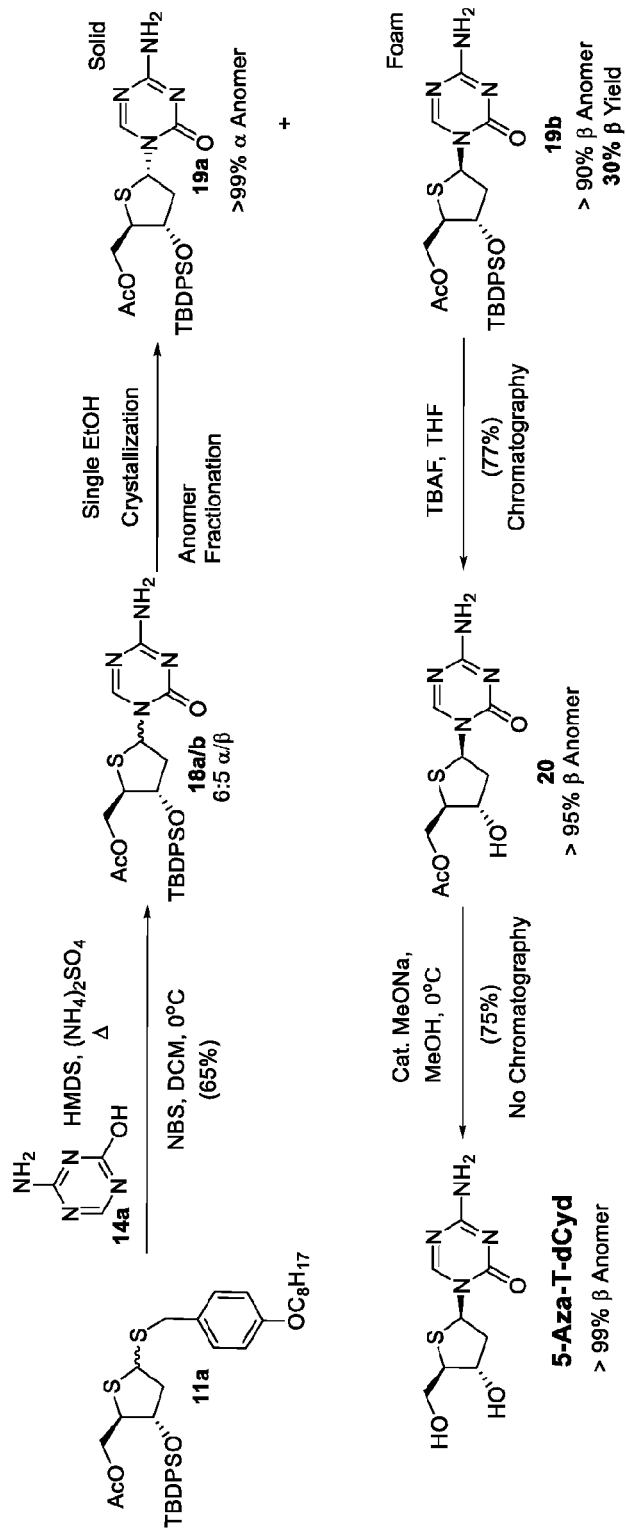
FIG. 5 is a synthetic scheme showing another route for making 5-aza-T-dCyd.

The Drug Synthesis and Chemistry Branch of the National Cancer Institute developed a synthetic route for preparing 5-aza-4'-thio-2'-deoxycytidine (5-aza-T-dCyd). As shown in FIG. 4, the diol is converted to a cyclic tetraisopropyldisilyloxy derivative having an acetyl group at the 1' position, which is then coupled with 5-azacystosine (MeCN) in the presence of trimethylsilyl trifluoromethanesulfonate (TMSOTf), hexamethyldisilazane (HMDS) and trimethylsilyl chloride (TMSCl) to give a 90% yield of α- and β-isomers in a ratio of about 5:3, respectively. Supercritical fluid chromatographic (SFC) separation afforded the desired β-isomer in 25% overall yield. Removal of the tetraisopropyldisilyloxy protecting group was achieved with ammonium fluoride in hot methanol to provide 5-aza-T-dCyd. Final deprotection with tetrabutylammonium fluoride provides 5-aza-T-dCyd (https://dtp.cancer.gov/organization/dscb/smchemistry/tdyd.htm, updated Jun. 17, 2015). Another alternative route utilized a 5'-acetyl,3-t-butyldphenylsilyloxy protected diol having an 4-octyloxybenzylthio at the 1' position of the sugar (11a, FIG. 5). Coupling 11a with silylated aza-cytosine in the presence of NBS (DCM, 0° C.) afforded a 60% yield of the target anomeric mixture with an α:β ratio of 6:5. Fractionation of the α and β anomers is achieved via fractional crystallization from absolute ethanol to give a 30% yield of 90% pure β anomer. Sequential deprotection with tetrabutylammonium fluoride (THF, 77%) followed by solvolysis in presence of catalytic methanolic sodium methoxide afforded pure 5-aza-T-dCyd. Yet another route utilizing a benzoyl protected diol having (4-octyloxybenzyl)thio group at the 1' position with coupling in the presence of 4'-benzoylcytosine and N-iodosuccinimide produced a 60% yield of a 6:5 mixture of α- and β-anomers. This synthesis could not be scaled up effectively as the coupling reaction lacked consistency (https://dtp.cancer-.gov/organization/dscb/smchemistry/tdyd.htm, updated Jun. 17, 2015).

Figure 7:
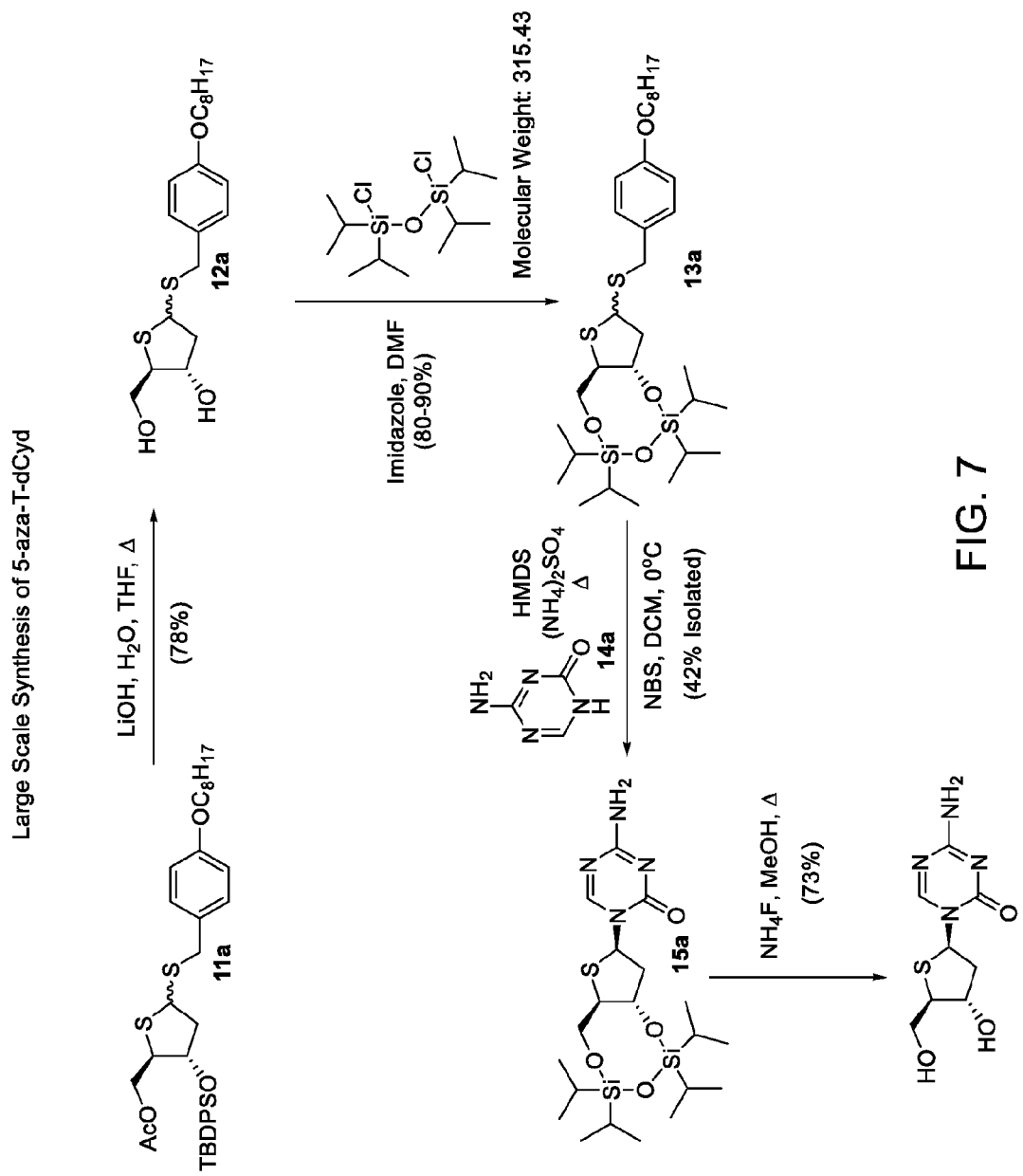
FIG. 7 is an exemplary synthetic scheme according to the present disclosure for making 5-aza-T-dCyd.

In contrast to the foregoing methods, the inventors surprisingly found that a combination of (i) the —SR$^1$ group, (ii) the 8-membered silylcycle formed with R$^2$, and (iii) use of NBS as the promoter provided the desired β:α stereoselectivity with preferential formation of the β-anomer and a higher isolated yield compared to other syntheses. In some examples (e.g., as shown in FIG. 7), when preparing 5-aza-T-dCyd, the (3/a ratio was as high as 7:1. In some embodiments, an isolated yield of pure, protected β-anomer up to 60% can be obtained. While isolated yields can range from 25-55% it can be expected that isolated yields will more typically fall in the range of 35-45% (see, e.g., FIG. 6). In contrast, other methods provide a much lower β:α selectivity, often with a β:α ratio of less than 1, and a much lower isolated yield. Consequently, the isolated yields from other methods are typically in the range from 10-25% of pure protected β anomer. Advantageously, the high selectivity for the β-anomer in combination with the increased yield facilitates separation of the anomers by conventional silica gel chromatography without the need for expensive separation techniques such as supercritical fluid chromatography. It is estimated that embodiments of the disclosed synthesis will reduce the manufacturing cost of the β-anomer by up to 60% relative to less stereoselective synthesis methods that provide a lower yield and/or require expensive purification techniques.

III. EXAMPLES

A general approach to stereoselective synthesis of a 2'-deoxynucleoside is illustrated in Scheme 1 (FIG. 1).

Synthesis of Thiosugar 8

Figure 2:
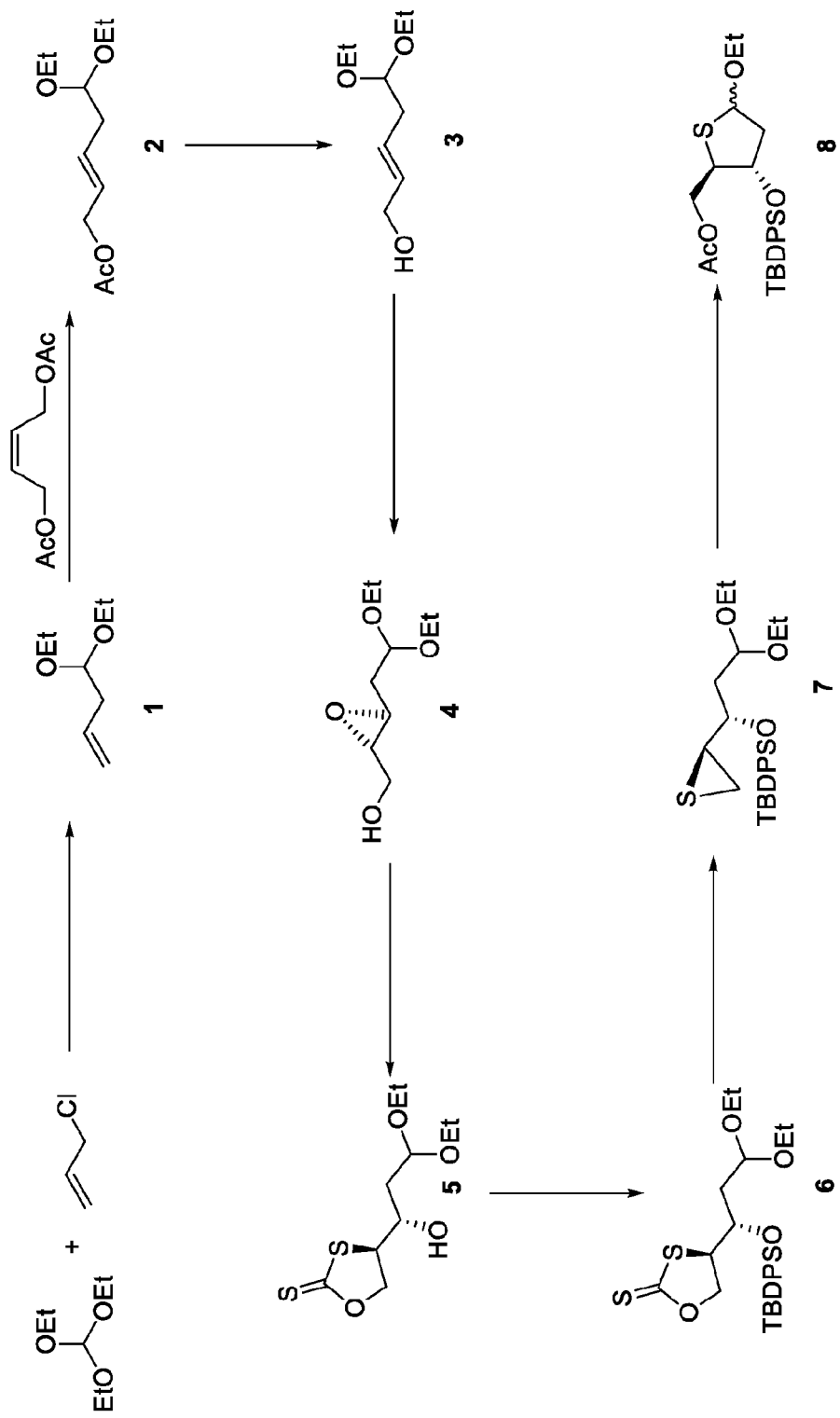
FIG. 2 is an exemplary synthetic scheme for making a thiosugar.

Scheme 2 shows one synthesis of a thiosugar (FIG. 2). Details of the synthesis are as follows.

Preparation of 4,4-Diethyoxybut-1-ene (1)

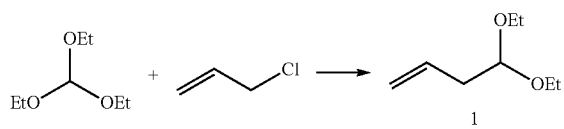

An adaptation of the method reported by Cloux, R.; Schlosser, M. *Helv. Chim. Acta.* 1984, 67, 1470-1474. To a mixture of magnesium (grit, ≥99.0% (KT) (Aldrich: 63040-250G-F) (31.8 g, 1307 mmol) and triethoxymethane (123 ml, 738 mmol) was added 3-chloroprop-1-ene (53.2 ml, 653 mmol) via addition funnel at a rate of 1 drop every 4 seconds, keeping the temperature under 105° C. The reaction mixture was vigorously stirred with an overhead stirrer. After addition was complete, the mixture was allowed to cool to room temperature overnight (14 hr). The reaction mixture was then chilled to 0° C., treated with saturated $NH_4Cl$ solution (200 mL), and stirred vigorously for 90 min. The aqueous layer was then extracted (even though Mg still remained) with $Et_2O$ (3×150 mL). The organic layers were combined, dried ($MgSO_4$), and concentrated, resulting in a clear and colorless residue. (It was observed that the Mg was completely quenched after 4 hr from the addition of $NH_4Cl$ making it safer to extract the aqueous layer.) To the clear residue was added a solution of acetic acid (20 ml, 349 mmol), sodium acetate (10 g, 122 mmol), and water (50 ml, 2775 mmol). The mixture was stirred for 2.5 hr. Sodium bicarbonate (32.4 g, 386 mmol) and water (about 200 mL) was then slowly added to the mixture. When evolution of $CO_2$ stopped, the aqueous layer was extracted with $Et_2O$ (2×150 mL). The organic layers were combined, dried ($MgSO_4$), and concentrated to afford 4,4-diethoxybut-1-ene (1) (80.6 g, 559 mmol, 86% yield) as clear and colorless liquid. $^1H$ NMR (400 MHz, chloroform-d) δ 5.86-5.75 (m, 1H); 5.14-5.06 (m, 1H); 4.54-4.51 (m, 1H); 3.66-3.62 (m, 2H); 3.55-3.49 (m, 2H); 1.23-1.19 (m, 6H).

Preparation of (E)-5,5-Diethoxypent-2-en-1-yl Acetate (2)

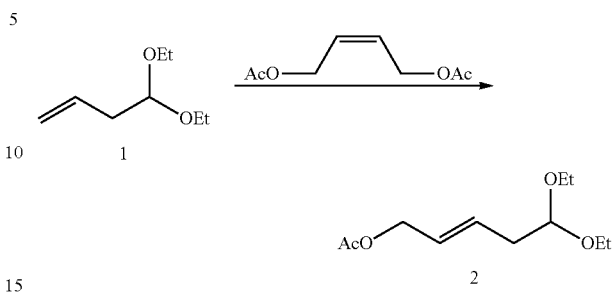

To a solution of 4,4-diethoxybut-1-ene (1) (2 g, 13.87 mmol) and (Z)-but-2-ene-1,4-diyl diacetate (8.84 ml, 55.5 mmol) in $CH_2Cl_2$ (34.7 ml) was added Grubb's II catalyst (0.235 g, 0.277 mmol). The reaction mixture was heated to 45° C. for 14 hr. The reaction mixture was allowed to cool to room temperature. TLC showed the possible formation of product. The reaction mixture's solvent was then removed to afford a black residue. The residue was loaded onto a 32-gram cartridge and purified using an 80 gram RediSep® Rf Gold Silica Gel column (Teledyne Isco, Lincoln, Nebr.), eluting with a 0-10% EtOAc/hexanes gradient, on a CombiFlash® chromatography system (Teledyne Isco). Fractions 6-16 were collected and concentrated to afford (E)-5,5-diethoxypent-2-en-1-yl acetate (2) (2.6 g, 12.02 mmol, 87% yield) as a clear light brown oil. $^1H$ NMR (400 MHz, chloroform-d) δ 5.81-5.58 (m, 2H), 4.67-4.45 (m, 3H), 3.63 (dq, J=9.3, 7.0 Hz, 2H), 3.48 (dq, J=9.4, 7.1 Hz, 2H), 2.46-2.34 (m, 2H), 2.04 (s, 3H), 1.18 (t, J=7.1 Hz, 6H).

Preparation of (E)-5,5-Diethoxypent-2-en-1-ol (3)

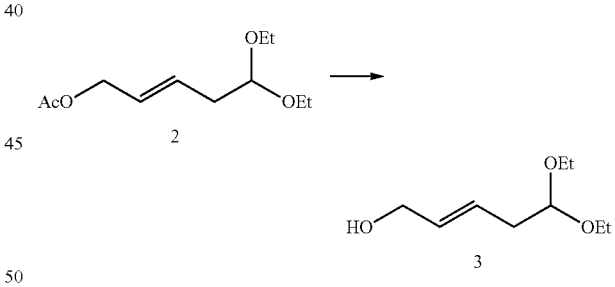

To a solution of (E)-5,5-diethoxypent-2-en-1-yl acetate (2) (2.6 g, 12.02 mmol) in MeOH (35 ml) was added potassium carbonate (0.831 g, 6.01 mmol). The reaction mixture was stirred overnight (16 hr) at room temperature. The reaction mixture was diluted with water (100 mL) and 2:1 EtOAc/Hex (100 mL). The layers were separated and the aqueous layer was extracted with 2:1 EtOAc/Hex (2×70 mL). The organic layers were combined, dried (MgSO4), and concentrated to afford a clear, slightly brown oil. The oil was purified using a 12-gram loading cartridge and 24-gram gold RediSep® silica gel column and eluting with 0-10% EtOAc/hexanes, on a CombiFlash® chromatography system. Fractions 2-16 were collected and concentrated to afford (E)-5,5-diethoxypent-2-en-1-ol (3) (1.4 g, 8.03 mmol, 66.8% yield) as a clear and colorless oil. $^1H$ NMR (400 MHz, chloroform-d) δ 5.72-5.70 (m, 2H), 4.59-4.50 (m, 1H), 4.12-4.10 (m, 2H), 3.68-3.63 (m, 2H), 3.53-3.49 (, 2H), 2.42-2.38 (m, 2H), 1.23-1.19 (m, 6H).

Preparation of ((2S,3S)-3-(2,2-Diethoxyethyl)oxiran-2-yl)methanol (4)

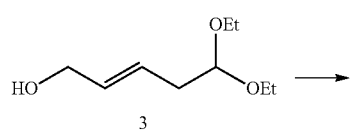

3

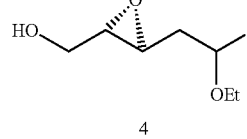

4

A 5,000 mL three neck round bottom flask under nitrogen was charged with activated molecular sieves, 4 A (60 g, 287 mmol) that had been stored at 75° C. The flask was thoroughly flame-dried and was placed under high vacuum (2-4 mm of Hg) overnight. The flask was placed under nitrogen atmosphere and was charged with DCM (dichloromethane), anhydrous (2000 mL). The suspension was cooled to −23° C. via immersion cooler and was treated successively with titanium (IV) isopropoxide (8.50 mL, 28.7 mmol) and diethyl L-tartrate (5.90 mL, 34.4 mmol). The mixture was treated rapidly dropwise with tert-butyl hydroperoxide (115 mL, 574 mmol) and the reaction was stirred 40 minutes while the catalyst mixture "aged". The reaction mixture was treated slowly dropwise with (E)-5,5-diethoxypent-2-en-1-ol (3) (50 g, 287 mmol) diluted to 500 mL volume with anhydrous DCM. (2-2.5 h). After stirring for 5 h at −22° C. after addition commenced, thin-layer chromatography (50% EtOAc/hexane) indicated complete consumption of starting material. The reaction was stirred for a total of 18 h at −22° C. The reaction was quenched with 23 mL of a 10% aqueous solution of NaOH in saturated sodium chloride. After adding 250 mL diethyl ether, the reaction was removed from the cooling bath and stirred while it warmed to 10° C. After stirring for 30 minutes, the mixture was treated with magnesium sulfate (23 g, 191 mmol) followed by 3 g Celite® diatomaceous earth (Imerys Filtration, San Jose, Calif.). After stirring for 15 minutes the mixture was passed through a pad of Celite® diatomaceous earth and the filter cake was washed with 500 mL diethyl ether. The filtrate was concentrated in vacuo to one liter in volume (~1:1 diethyl ether/DCM). The mixture was cooled to 0° C., was treated drop-wise with trimethyl phosphite (37.3 mL, 316 mmol), and was stirred 30 minutes at 0° C. The mixture was diluted with 300 mL brine. The milky suspension was filtered through a bed of Celite® diatomaceous earth to help effect phase separation. The aqueous layer was washed with 200 mL diethyl ether and the combined organic layer was washed with 300 mL brine. The organic layer was dried over anhydrous magnesium sulfate and was concentrated in vacuo to give 89.4 g (54% pure, 88% calculated yield) of a pale oil. H-NMR indicated slightly better than a 1:1 mixture of epoxide and dimethyl phosphate along with t-butanol and other minor impurities. ¹H NMR (400 MHz, chloroform-d) δ 4.65 (m, 1H), 3.88 (m, 1H), 3.62 (m, 2H), 3.50 (m, 2H), 3.05 (m, 1H), 2.94 (m, 1H), 1.91 (m, 2H), 1.84-1.71 (m, 2H), 1.19 (m, 6H).

Preparation of (R)-4-((S)-3,3-diethoxy-1-hydroxypropyl)-1,3-oxathiolane-2-thione (5)

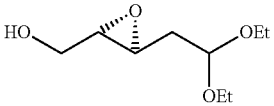

4

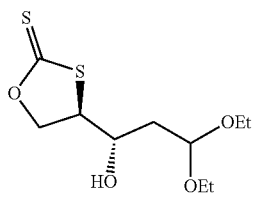 + 

5                                    5a

An oven-dried 250 mL two-neck round bottom flask under nitrogen was charged with carbon disulfide (60.3 mL, 1001 mmol), dry tetrahydrofuran (475 mL, 5797 mmol) and ((2S,3S)-3-(2,2-diethoxyethyl)oxiran-2-yl)methanol (4) (47.6 g, 250 mmol) and the solution was cooled to −78° C. The colorless solution was treated drop-wise with sodium bis(trimethylsilyl)amide in THF (300 mL, 300 mmol) (~1 h addition). The deep orange solution was stirred at −78° C. for 30 minutes. The reaction was stirred for a total of 2 h and was quenched at −78° C. with acetic acid (17.90 mL, 313 mmol). The reaction then was stirred without the bath until it warmed to −30° C., was treated with 225 g silica gel (230-400 mesh) and the mixture was concentrated to dryness overnight. The crude plug (placed in a CombiFlash® dry load cartridge was eluted directly onto a 340 G UltraSphere™ SNAP cartridge, with a 0-60% EtOAc/hexane gradient into 27 mL fractions. Fractions 54-138 were combined and concentrated to afford 53.10 g (80%) of (R)-4-((S)-3,3-diethoxy-1-hydroxypropyl)-1,3-oxathiolane-2-thione (5) as an amber oil. Fractions 27-40 were combined and concentrated to afford 10.1 g (12%) of (R)-4-((S)-3,3-diethoxy-1-((trimethylsilyl)oxy)propyl)-1,3-oxathiolane-2-thione (5a) as a deep yellow oil. TMS ether (5a) (10.15 g, 30.0 mmol) was dissolved in methanol (110 mL) in a 500 mL one neck round bottom flask. The solution was treated with acetic acid (5.4 ml, 94 mmol) and the reaction was stirred for 19 h at room temperature. The reaction was diluted with 200 mL toluene and was concentrated to afford an additional 8.0 g (12%) the title compound (5) as a dark yellow oil. Alcohol 5: 1H NMR (400 MHz, chloroform-d) δ 5.16-5.08 (m, 1H), 4.87-4.78 (m, 1H), 4.69 (m, 1H), 4.04-3.87 (m, 3H), 3.69 (m, 2H), 3.58-3.43 (m, 2H), 1.90 (m, 1H), 1.88-1.73 (m, 1H), 1.20 (m, 6H). TMS ether 5a: 1H NMR (400 MHz, chloroform-d) δ 4.93 (m, 1H), 4.76 (m, 1H), 4.61 (m, 1H), 4.10 (m, 1H), 3.97 (m, 1H), 3.68-3.52 (m, 2H), 3.51-3.38 (m, 2H), 1.90 (m, 1H), 1.79 (m, 1H), 1.26 (s, 1H), 1.25-1.13 (m, 6H), 0.15 (d, J=0.7 Hz, 9H).

Preparation: (R)-4-((S)-1-((tert-Butyldiphenylsilyl)oxy)-3,3-diethoxypropyl)-1,3-oxathiolane-2-thione (6)

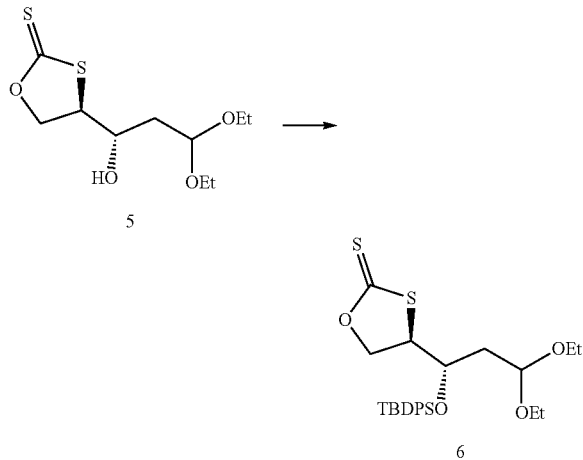

(R)-4-((S)-3,3-Diethoxy-1-hydroxypropyl)-1,3-oxathiolane-2-thione (5) (11.78 g, 44.2 mmol) was dissolved in DMF (dimethylformamide, 44 mL, 568 mmol) in a 500 mL one-neck round bottom flask under nitrogen. The solution was treated with imidazole (7.53 g, 111 mmol) in a single portion followed by tert-butylchlorodiphenylsilane (TBDPS) (23.00 ml, 88 mmol) and the reaction was stirred for 72 h. The mixture was diluted with 200 mL EtOAc, was stirred vigorously with 100 mL 50% saturated 1:1 sodium bicarbonate/sodium chloride for 10 minutes, and the layers were separated. The organic layer was washed with 3×50 mL 50% saturated sodium chloride, was dried over anhydrous magnesium sulfate and was concentrated in vacuo to give an amber oil. The crude material was dissolved in hexane and was loaded onto a 50 G UltraSil® SNAP cartridge. The column was eluted over a 100 G UltraSil® SNAP cartridge with a 0-10% EtOAc/hexane gradient while collecting 27 mL fractions on a Biotage® system (Uppsala, Sweden). Fractions 13-52 were combined and concentrated to afford 19.28 g (86%) of (R)-4-((S)-1-((tert-butyldiphenylsilyl)oxy)-3,3-diethoxypropyl)-1,3-oxathiolane-2-thione (6) as a golden oil. 1H NMR (400 MHz, Chloroform-d) δ 7.74-7.60 (m, 4H), 7.50-7.32 (m, 6H), 4.82 (m, 1H), 4.70 (m, 1H), 4.46 m, 1H), 4.23 (m, 1H), 4.04 (m, 1H), 3.50-3.22 (m, 3H), 3.12 (m, 1H), 1.90 (m, 1H), 1.72 (m, 1H), 1.11 (m, 3H), 1.05 (s, 9H), 1.10-0.92 (m, 6H).

Preparation of tert-Butyl((S)-3,3-diethoxy-1-((S)-thiiran-2-yl)propoxy)diphenylsilane (7)

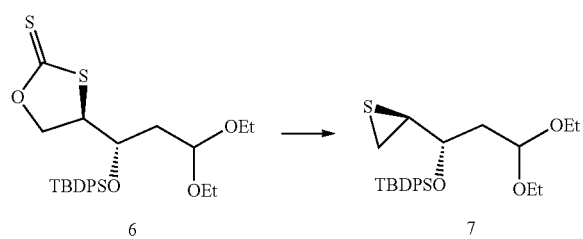

(R)-4-((S)-1-((tert-Butyldiphenylsilyl)oxy)-3,3-diethoxypropyl)-1,3-oxathiolane-2-thione (6) (11.9 g, 23.57 mmol) was dissolved in methanol anhydrous (140 mL, 3460 mmol) in a 250 mL one-neck round bottom flask under nitrogen and the mixture was cooled to 0° C. The yellow solution was treated with powdered potassium carbonate 325 mesh (3.75 g, 27.1 mmol) and the reaction was stirred 3 h @ 0° C. The mixture was diluted with 500 mL 1:1 diethyl ether/hexane, the insoluble material was removed by filtration through anhydrous potassium carbonate, and the filtrate was concentrated in vacuo to a yellow oil. The crude material was dissolved in a minimum amount of hexane, was loaded onto a 50 G UltraSphere® SNAP cartridge and was eluted with a 0-4% EtOAc/hexane gradient into 27 mL fractions on a Biotage® system. Fractions 3-11 were combined and concentrated in vacuo to afford 9.67 g (92%) of tert-butyl((S)-3,3-diethoxy-1-((S)-thiiran-2-yl)propoxy)diphenylsilane (7) as a colorless oil. 1H NMR (400 MHz, chloroform-d) δ 7.71 (m, 4H), 7.47-7.32 (m, 6H), 4.91 (m, 1H), 3.66-3.28 (m, 5H), 2.90 (m, 1H), 2.12-2.00 (m, 2H), 1.84 (m, 1H), 1.52 (m, 1H), 1.16 (m, 6H), 1.02 (s, 9H).

Preparation of ((2R,3S)-3-((tert-Butyldiphenylsilyl)oxy)-5-ethoxytetrahydrothiophen-2-yl)methyl Acetate (8)

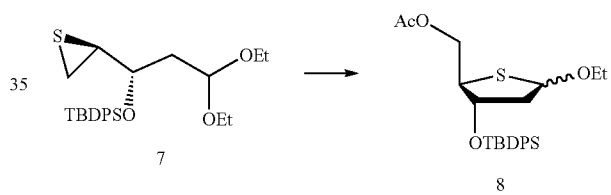

tert-Butyl((S)-3,3-diethoxy-1-((S)-thiiran-2-yl)propoxy)diphenylsilane (7) (9.67 g, 21.74 mmol) was dissolved in a mixture of acetic acid (25 mL, 437 mmol) and acetic anhydride (30 mL, 318 mmol) in a 250 mL one-neck round bottom flask under nitrogen. The solution was treated with potassium acetate (10.67 g, 109 mmol) and was placed in a 120° C. oil bath for 4 h. The mixture was cooled, was diluted with 500 mL toluene, the solid material was removed by filtration, and the filtrate was concentrated to dryness. The residue was dissolved in a minimum amount of DCM, was loaded onto a 50 G UltraSphere® SNAP cartridge, and was eluted over a 100 g UltraSil® SNAP cartridge with a 0-5% EtOAc/hexane gradient (0-25% of a 20% EtOAc/hexane stock solution) into 27 mL fractions on a CombiFlash® system. Fractions 10-28 were combined and concentrated to afford 8.6 g (86%) of ((2R,3S)-3-((tert-butyldiphenylsilyl)oxy)-5-ethoxytetrahydrothiophen-2-yl)methyl acetate (8) as 3:2 anomeric mixture as a pale oil. 1H NMR (400 MHz, chloroform-d) δ 7.71-7.59 (m, 4H), 7.46-7.33 (m, 6H), 5.15 (m, 1H), 4.50-4.15 (m, 1H), 4.04 (m, 1H), 3.87 (m, 1H), 3.72-3.58 (m, 1H), 3.56-3.47 (m, 1H), 3.26 (m, 1H), 2.29-2.06 (m, 2H), 1.88 (m, 3H), 1.16 (m, 3H), 1.05 (s, 9H).

Synthesis of 4-Octyloxyphenylmethane Thiol 10

Scheme 3 shows one synthesis of 4-octyloxyphenylmethane thiol (FIG. 3). Details of the synthesis are as follows.

Preparation of 4-Octyloxyphenylmethanol (9):

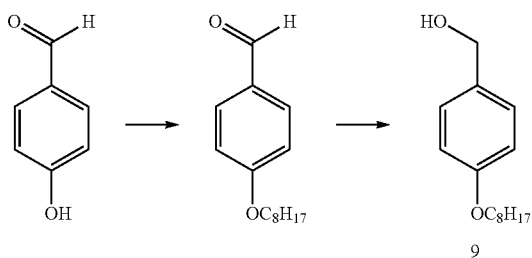

A mixture of 4-hydroxybenzaldehyde (430.0 g, 3.521 mol), 1-bromooctane (714.9 g, 3.701 mol) and potassium carbonate (515.7 g, 3.731 mol) in acetonitrile (3.4 L) was refluxed overnight and cooled to ambient temperature. The solid was filtered off, and filtrate was concentrated under the reduced pressure to give 848.3 g (102.8%) of crude 4-octyloxybenzaldehyde. Product was dissolved in methanol (2.6 L). Sodium borohydride (44.4 g, 1.173 mol) was added portion wise to the formed solution keeping the temperature below 15° C. The reaction mixture was stirred at ambient temperature for 1 h. A solution of NaOH (14.33 g, 358.3 mmol) in water (200 mL) was added followed by ethyl acetate (1.7 L) and brine (0.5 L). The organic solution was separated, dried over sodium sulfate and evaporated under the reduced pressure. Heptane (1 L) was added to the residue. The formed mixture was cooled to 4° C. Solid was filtered off, washed with ice cool heptane and dried in vacuum to give 765.4 g (91.9%) of crude 4-octyloxyphenylmethanol 9, which was used in the following step without further purification. $^1$H NMR spectrum (300 MHz, CDCl$_3$/TMS): δ 7.26 (m, 2H), 6.87 (m, 2H), 4.59 (s, 2H), 3.95 (m, 2H), 1.78 m, 3H), 1.47-1.29 (m, 10H), 0.89 (m, 3H).

Preparation of 4-Octylphenylmethanethiol (10):

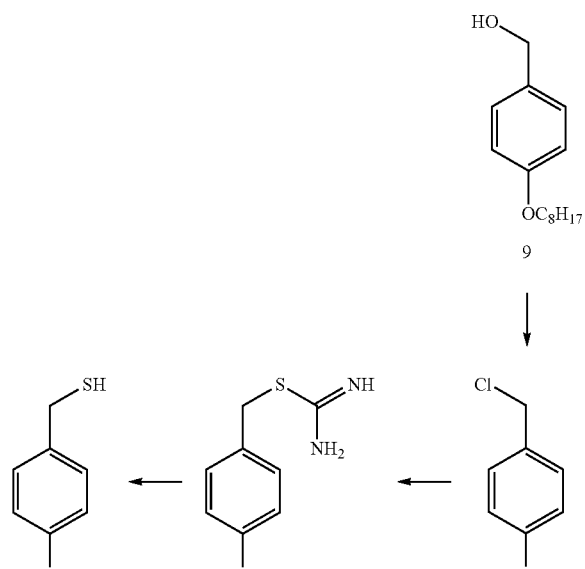

A mixture of 4-octyloxyphenylmethanol (9) (765.42 g, 3.238 mol), concentrated HCl (600 mL) and acetonitrile (1.7 L) was stirred overnight at ambient temperature. Thiourea (296.0 g, 3.888 mol) and acetonitrile (600 mL) were added. The mixture was heated to reflux for 2 h, cooled to room temperature and kept overnight. A solution of sodium hydroxide (518.7 g, 12.967 mol) in water (1 L) was added. The mixture was heated to reflux for 3 h and cooled to 10° C. Concentrated HCl (600 mL) was added keeping the temperature below 15° C. The mixture was extracted with MTBE (3 L). The extract was dried over magnesium sulfate and concentrated under the reduced pressure. Heptane (1 L) was added to the residue, and the mixture was evaporated. Heptane (1.5 L) was added to the residue. The milky solution was kept overnight and filtered through a silica gel pad (500 g). The filtrate was evaporated to give 679.2 g (83.1%) of 4-octyloxyphenylmethanethiol (10) as a colorless oil. $^1$H NMR spectrum (300 MHz, CDCl$_3$/TMS): δ 7.23 (m, 2H), 6.84 (m, 2H), 3.95 (m, 2H), 3.66 (m, 2H), 1.77 (m, 3H), 1.21-1.59 (m, 10H), 0.88 (m, 3H).

Synthesis of Coupling Partners 13a-h:

Preparation of ((2R,3S)-3-((tert-Butyldiphenylsilyl)oxy)-5-((4-octyloxybenzyl)thio)-tetrahydrothiophen-2-yl)methyl Acetate (11a). General Method A

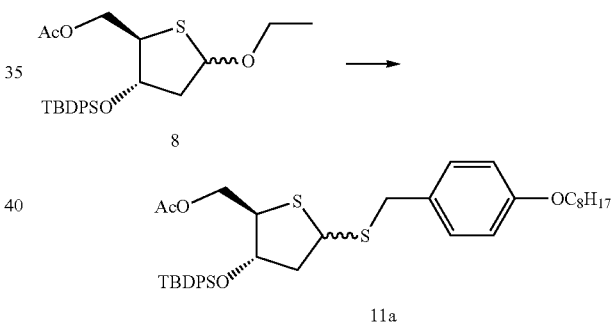

Boron trifluoride diethyl etherate (278.32 g, 1.961 mol) was added drop wise under argon to a stirred solution of compound 8 (455.5 g, 980.5 mmol) and 4-octyloxyphenylmethanethiol (10) (252.42 g, 1.0 mol) in anhydrous DCM (4.6 L) at −1 to 0° C. The reaction mixture was stirred at this temperature for 2 h. Triethylamine (238.12 g, 2.353 mol) was added drop-wise keeping the temperature under 5° C. followed by water (2 L). The reaction mixture was stirred for 1 h. The organic solution was separated, dried over magnesium sulfate and evaporated. The residue was purified by column chromatography (silica gel, ethyl acetate/heptanes, 1:15, then 1:9, and then 1:4) to give 486.9 g (74.7%) of ((2R,3S)-3-((tert-butyldiphenylsilyl)oxy)-5-((4-octyloxybenzyl)thio)-tetrahydrothiophen-2-yl)methyl acetate (11a) as a pale oil. $^1$H NMR spectrum (300 MHz, CDCl$_3$/TMS): δ 7.59-7.79 (m, 4H), 7.35-7.45 (m, 6H), 7.2 (m, 2H), 6.82 (m, 2H), 4.57 (m, 0.7H), 4.45 (m, 0.7H), 4.04-4.22 (m, 0.4H), 3.85-3.95 (m, 3H), 3.65-3.85 (m, 2.4H), 3.5 (m, 1H), 2.0-2.25 (m, 1H), 1.87 (m, 3H), 1.75 (m, 2H), 1.24-1.50 (m, 10H), 1.06 (m, 9H), 0.87 (m, 3H).

Preparation of (4S,5R)-4-Hydroxy-5-hydroxymethyl-2-((4-(octyloxy)benzyl)thio)-tetrahydrothiophene, (12a) NSC-D776760-N General Method B

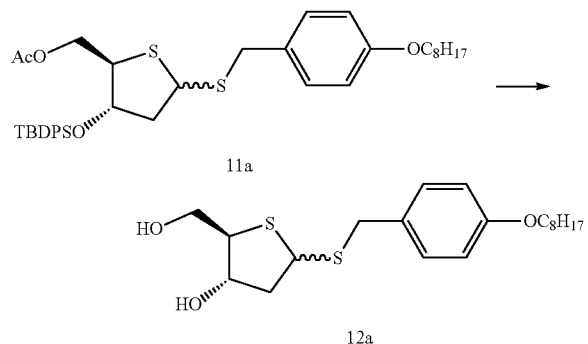

A mixture of solution of compound 11a (492.1 g, 739.9 mmol) in THF (5.7 L) and a solution of lithium hydroxide monohydrate (310.46 g, 7.399 mol) in water (1.9 L) was heated to reflux for 70 h. The mixture was cooled to ambient temperature and MTBE (2 L) was added. Organic solution was separated. Aqueous layer was extracted with MTBE (1 L). Combined organic solutions were dried over sodium sulfate and evaporated to give 485.5 g of crude product. It was dissolved under heating in heptanes (3 L). The formed solution was cooled to ambient temperature, and then to 0° C. overnight. The formed solid was filtered off, washed with heptanes (0.5 L, −5° C.) and dried under vacuum to give 212.0 g (75%) of (4S,5R)-4-hydroxy-5-hydroxymethyl-2-((4-(octyloxy)benzyl)thio)-tetrahydrothiophene (12a). The filtrate was evaporated. The residue was purified by column chromatography (silica gel, ethyl acetate/heptanes, 1:9, then 1:4, and then 7:3) to give an additional 10.2 g (3.6%) of compound 12a. The two crops of target compound were combined to afford 222.2 g (78.1%) of compound 12a. $^1$H NMR spectrum (300 MHz, CDCl$_3$/TMS): δ 7.21 (d, J=8.5 Hz, 2H), 6.84 (d, J=8.5 Hz, 2H), 4.57 (m, 1H), 4.36 (t, J=6.3 Hz, 1H), 3.93, (t, J=6.6 Hz, 2H), 3.43-3.83 (m, 4H), 3.45 (m, 1H), 2.13-2.40 (m, 4H), 1.77 (m, 2H), 1.20-1.50 (m, 10H), 0.89 (m, 3H).

Preparation of (6aR,9aS)-2,2,4,4-tetraisopropyl-8-((4-(octyloxy)benzyl)thio)tetrahydro-6H-thieno[3,2-f][1,3,5,2,4]trioxadisilocine (13a). General Method C

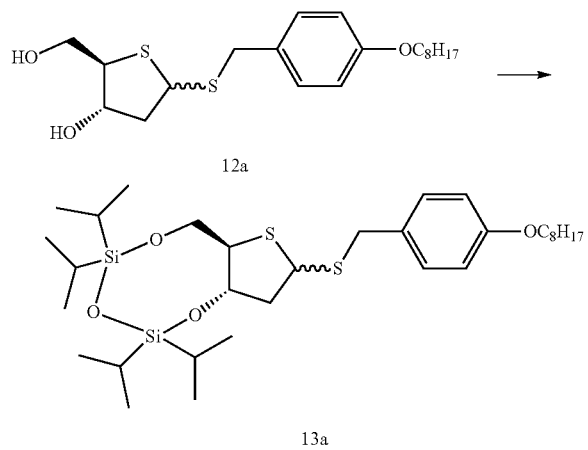

(2R,3S)-2-(Hydroxymethyl)-5-((4-(octyloxy)benzyl)thio)tetrahydrothiophen-3-ol (12a) (5 g, 13.00 mmol) was combined with 1H-imidazole (2.213 g, 32.5 mmol) in dry N,N-dimethylformamide (25 mL, 13.00 mmol) in a 100 mL one-neck round-bottom flask under nitrogen. The solution was cooled to 0° C., was treated with 1,3-dichloro-1,1,3,3-tetraisopropyldisiloxane (5.82 mL, 18.20 mmol), and the reaction was stirred overnight as the cooling bath expired. The mixture was diluted with 125 mL EtOAc and was washed with 60 mL 50% saturated 1:1 sodium chloride/sodium bicarbonate followed by 3×50 mL 50% saturated sodium chloride. The organic layer was dried over anhydrous magnesium sulfate and was concentrated in vacuo to give 11 grams of a pale oil. The crude material was dissolved in hexane, was loaded onto a 50 g UltraSil® SNAP cartridge and was eluted with a 0-4% EtOAc/hexane gradient (0-20% of a 20% EtOAc/hexane EtOAc phase) on a CombiFlash® system. Fractions 2-13 were combined and concentrated to afford 7.37 g (90%) of (6aR,9aS)-2,2,4,4-tetraisopropyl-8-((4-(octyloxy)benzyl)thio)tetrahydro-6H-thieno[3,2-g][1,3,5,2,4]trioxadisilocine (13a) as a colorless oil. $^1$H NMR (400 MHz, chloroform-d) δ 7.20 (m, 2H), 6.81 (m, 2H), 4.59 (m, 0.2H), 4.22 (m, 2H), 4.05 (m, 1), 3.91 (m, 2H), 3.76-3.86 (m, 3H), 3.44 (m, 0.8H), 3.33 (m, 0.2), 2.5 (m, 0.8H), 2.18-2.40 (m, 0.4H), 2.00 (m, 0.8H), 1.75 (m, 2H), 1.2-1.45 (m, 10H), 0.92-1.19 (m, 28H), 0.89 (m, 3H).

Preparation of ((2R,3S)-5-(Benzylthio)-3-((tert-butyldiphenylsilyl)oxy)tetrahydrothiophen-2-yl) methyl Acetate (11b)

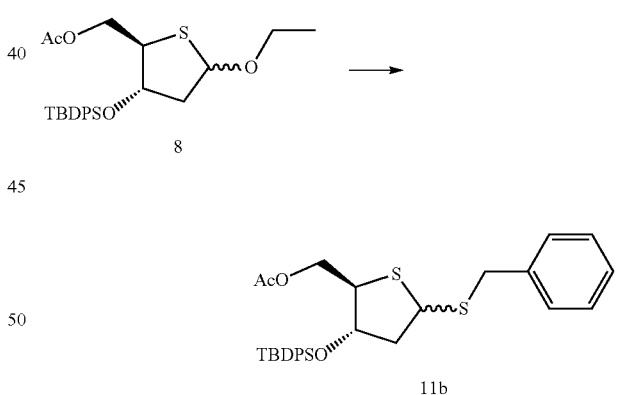

((2R,3S)-3-((tert-butyldiphenylsilyl)oxy)-5-ethoxytetrahydrothiophen-2-yl)methyl acetate (8) (3.6 g, 7.85 mmol) was reacted with phenylmethanethiol in the manner described in General Method A to afford 4.02 g (95%) of ((2R,3S)-5-(benzylthio)-3-((tert-butyldiphenylsilyl)oxy)tetrahydrothiophen-2-yl)methyl acetate (11b) as a colorless oil. $^1$H NMR (400 MHz, chloroform-d) δ 7.74-7.54 (m, 5H), 7.48-7.33 (m, 5H), 7.38-7.17 (m, 5H), 4.56 (m, 0.35H), 4.41 (m, 0.35H), 4.16 (m, 2H), 4.04 (m, 1H), 3.87 (m, 1H), 3.82-3.72 (m, 3H), 3.75-3.63 (m, 1H), 3.56-3.42 (m, 0.4H), 2.28-1.99 (m, 2H), 1.85 (m, 3H), 1.04 (m, 9H).

Preparation of (2R,3S)-5-(Benzylthio)-2-(hydroxymethyl)tetrahydrothiophen-3-ol (12b)

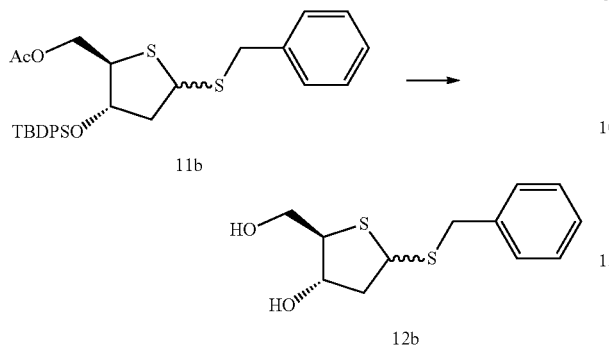

((2R,3S)-5-(Benzylthio)-3-((tert-butyldiphenylsilyl)oxy) tetrahydrothiophen-2-yl)methyl acetate (11b) (4.02 g, 7.49 mmol) was reacted with lithium hydroxide in the manner described in General Method B to afford 1.68 g (88%) of (2R,3S)-5-(benzylthio)-2-(hydroxymethyl)tetrahydrothiophen-3-ol (12b) a colorless viscous oil. $^1$H NMR (400 MHz, chloroform-d) δ 7.38-7.20 (m, 5H), 4.57 (m, 0.4H), 4.45-4.32 (m, 2H), 3.86 (m, 3H), 3.82-3.67 (m, 1H), 3.72-3.63 (m, 2H), 3.62-3.52 (m, 1H), 3.45 (m, 0.4H), 2.48-2.38 (m, 1H), 2.41-2.24 (m, 1H), 2.28-2.15 (m, 1H), 2.06 (m, 2H).

Preparation of (6aR,9aS)-8-(Benzylthio)-2,2,4,4-tetraisopropyltetrahydro-6H-thieno[3,2-f][1,3,5,2,4]trioxadisilocine (13b)

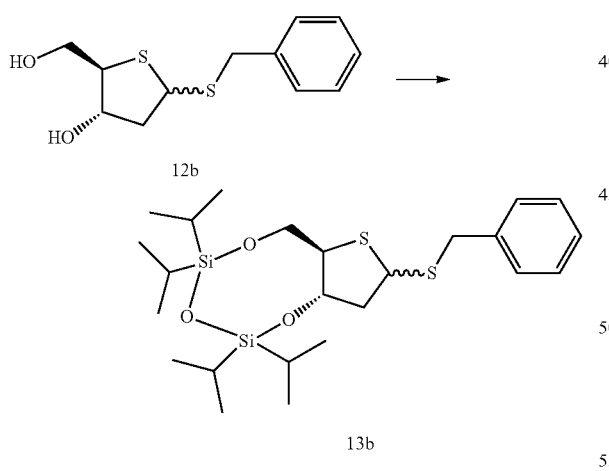

(2R,3S)-5-(benzylthio)-2-(hydroxymethyl)tetrahydrothiophen-3-ol (12b) was reacted with 1,3-dichloro-1,1,3,3-tetraisopropyldisiloxane (2.396 mL, 7.49 mmol) in the manner described in General Method C to afford 4.31 g (71%) of (6aR,9aS)-8-(benzylthio)-2,2,4,4-tetraisopropyltetrahydro-6H-thieno[3,2-f][1,3,5,2,4]trioxadisilocine (13b) as a colorless oil. $^1$H NMR (400 MHz, chloroform-d) δ 7.33-7.18 (m, 5H), 4.67 (m, 0.28H), 4.29-4.14 (m, 2H), 4.16-3.97 (m, 2H), 3.93-3.76 (m, 4H), 3.40 (m, 1H), 3.29 (m, 0.28H), 2.51 (m, 1H), 2.43-2.18 (m, 0.46H), 2.00 (m, 1H), 1.10-0.84 (m, 28H).

Preparation of ((2R,3S)-3-((tert-Butyldiphenylsilyl)oxy)-5-(phenylthio)tetrahydrothiophen-2-yl)methyl Acetate (11c)

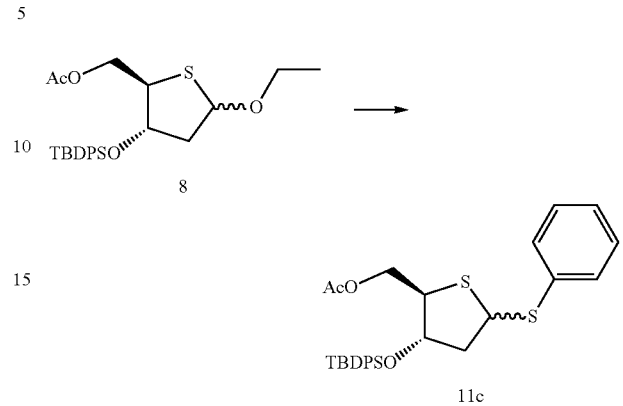

((2R,3S)-3-((tert-Butyldiphenylsilyl)oxy)-5-ethoxytetrahydrothiophen-2-yl)methyl acetate (8) (3.6 g, 7.85 mmol) was reacted with benzenethiol (0.806 mL, 7.85 mmol) in the manner described in General Method A to afford 3.63 g of ((2R,3S)-3-((tert-butyldiphenylsilyl)oxy)-5-(phenylthio)tetrahydrothiophen-2-yl)methyl acetate (11c) as a colorless oil. $^1$H NMR (400 MHz, Chloroform-d) δ 7.74-7.57 (m, 5H), 7.48-7.35 (m, 5H), 7.39-7.15 (m, 5H), 4.97 (m, 0.7H), 4.71 (m, 0.35H), 4.44 (m, 1H), 4.24 (m, 0.33H), 3.98 (m, 0.35H), 3.87-3.65 (m, 2H), 3.50 (m, 0.74H), 2.42-2.20 (m, 2H), 1.94-1.81 (m, 4H), 1.07 (m, 9H).

Preparation of (2R,3S)-2-(Hydroxymethyl)-5-(phenylthio)tetrahydrothiophen-3-ol (12c)

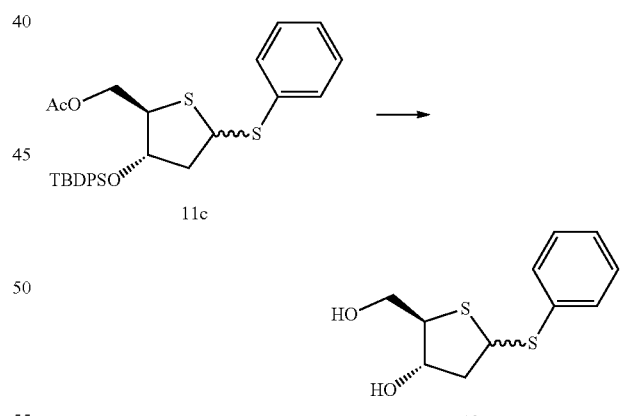

((2R,3S)-3-((tert-Butyldiphenylsilyl)oxy)-5-(phenylthio) tetrahydrothiophen-2-yl)methyl acetate (11c) (4.02 g, 7.69 mmol) was reacted with lithium hydroxide hydrate (1.841 g, 77 mmol) in the manner described in General Method B to afford 1.55 g (83%) of (2R,3S)-2-(hydroxymethyl)-5-(phenylthio)tetrahydrothiophen-3-ol (12c) as a viscous pale oil. $^1$H NMR (400 MHz, chloroform-d) δ 7.49-7.28 (m, 5H), 4.89-4.81 (m, 1H), 4.55 (dt, J=6.0, 4.5 Hz, 0.6H), 4.42 (m, 0.35H), 3.74-3.51 (m, 3H), 3.42 (m, 0.61H), 2.51-2.21 (m, 3H).

Preparation of (6aR,9aS)-2,2,4,4-tetra-Isopropyl-8-(phenylthio)tetrahydro-6H-thieno[3,2-f][1,3,5,2,4]trioxadisilocine (13c)

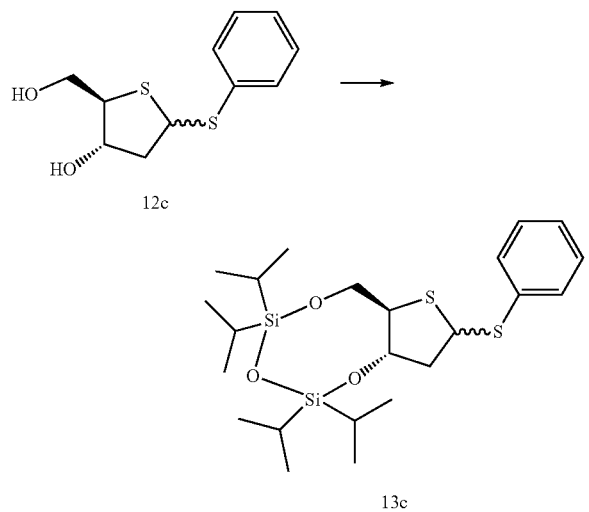

13c (2R,3S)-2-(Hydroxymethyl)-5-(phenylthio)tetrahydrothiophen-3-ol (12c) (1.55 g, 6.40 mmol) was reacted with 1,3-dichloro-1,1,3,3-tetraisopropyldisiloxane (2.455 mL, 7.67 mmol) in the manner described in General Method C to afford 2.55 g (82%) of (6aR,9aS)-2,2,4,4-tetra-Isopropyl-8-(phenylthio)tetrahydro-6H-thieno[3,2-f][1,3,5,2,4]trioxadisilocine (13c) as a colorless oil. $^1$H NMR (400 MHz, chloroform-d) δ 7.47-7.35 (m, 2H), 7.35-7.21 (m, 3H), 4.77-4.66 (m, 1H), 4.28 (m, 0.4H), 4.03 (m, 1H), 3.93-3.75 (m, 1H), 3.43-3.27 (m, 1H), 2.65 (m, 0.4H), 2.42-2.34 (m, 1H), 2.13 (m, 0.4H), 1.23-0.83 (m, 28H).

Preparation of ((2R,3S)-3-((tert-Butyldiphenylsilyl)oxy)-5-((4-ethoxybenzyl)thio)tetrahydrothiophen-2-yl)methyl Acetate (11d)

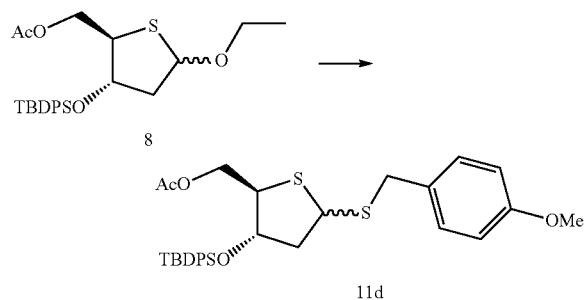

((2R,3S)-3-((tert-Butyldiphenylsilyl)oxy)-5-ethoxytetrahydrothiophen-2-yl)methyl acetate (8) (3.8 g, 8.28 mmol) was reacted with (4-methoxyphenyl)methanethiol (1.154 mL, 8.28 mmol) in the manner described in General Method A to afford 4.07 g of ((2R,3S)-3-((tert-butyldiphenylsilyl)oxy)-5-((4-methoxybenzyl)thio)tetrahydrothiophen-2-yl)methyl acetate (11d) as a colorless oil. $^1$H NMR (400 MHz, chloroform-d) δ 7.71-7.54 (m, 4H), 7.48-7.32 (m, 6H), 7.20 (m, 2H), 6.86-6.77 (m, 2H), 4.56 (m, 0.25H), 4.41 (m, 0.25H), 4.21-4.00 (m, 2H), 3.92-3.82 (m, 0.25H), 3.82-3.63 (m, 6H), 3.49 (m, 0.26H), 2.29-2.15 (m, 1H), 2.18-1.99 (m, 1H), 1.86 (m, 3H), 1.04 (m, 9H).

Preparation of (2R,3S)-2-(Hydroxymethyl)-5-((4-methoxybenzyl)thio)tetrahydrothiophen-3-ol (12d)

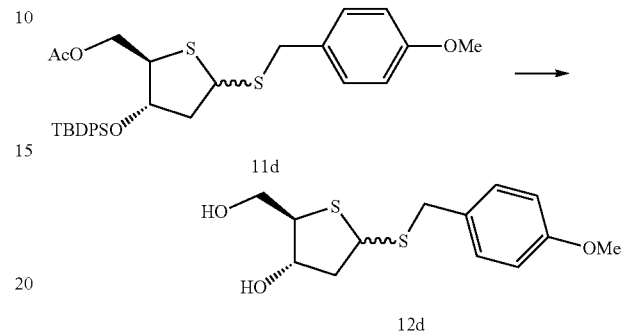

((2R,3S)-3-((tert-Butyldiphenylsilyl)oxy)-5-((4-methoxybenzyl)thio)tetrahydrothiophen-2-yl)methyl acetate (11d) (4.02 g, 7.09 mmol) was reacted with lithium hydroxide hydrate (1.698 g, 70.9 mmol) in the manner described in General Method C to afford 1.68 g (88%) of (2R,3S)-2-(hydroxymethyl)-5-((4-methoxybenzyl)thio)tetrahydrothiophen-3-ol (12d) as a white solid. $^1$H NMR (400 MHz, chloroform-d) δ 7.21 (m, 2H), 6.84 (m, 2H), 4.55 (m, 0.2H), 4.36 (m, 2H), 3.88-3.73 (m, 5H), 3.76-3.61 (m, 2H), 3.60-3.50 (m, 1H), 3.43 (m, 0.22H), 2.46-2.11 (m, 2H).

Preparation of (6aR,9aS)-2,2,4,4-tetraisopropyl-8-((4-methoxybenzyl)thio)tetrahydro-6H-thieno[3,2-f][1,3,5,2,4]trioxadisilocine (13d)

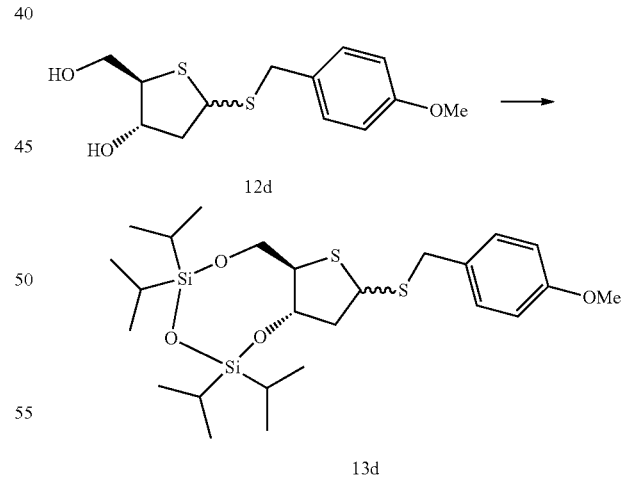

(2R,3S)-2-(Hydroxymethyl)-5-((4-methoxybenzyl)thio)tetrahydrothiophen-3-ol (12d) (1.6 g, 5.59 mmol) was reacted with 1,3-dichloro-1,1,3,3-tetraisopropyldisiloxane (2.145 mL, 6.70 mmol) in the manner described in General Method C to afford 1.52 g (51%) of (6aR,9aS)-2,2,4,4-tetraisopropyl-8-((4-methoxybenzyl)thio)tetrahydro-6H-thieno[3,2-f][1,3,5,2,4]trioxadisilocine (13d) as a colorless oil.

Preparation of ((2R,3S)-3-((tert-Butyldiphenylsilyl)oxy)-5-((4-methoxyphenyl)thio)tetrahydrothiophen-2-yl)methyl Acetate (11e)

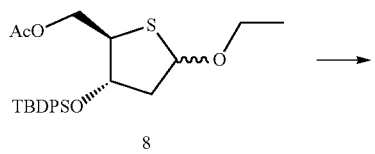

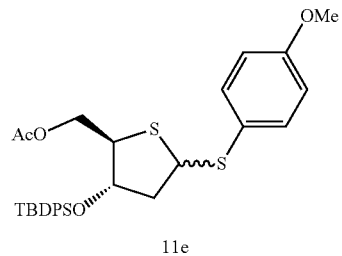

((2S,3R)-3-((tert-Butyldiphenylsilyl)oxy)-5-ethoxytetrahydrothiophen-2-yl)methyl acetate (8) (1.43 g, 3.12 mmol) was reacted with 4-methoxybenzenethiol (0.403 ml, 3.27 mmol) in the manner described in General Method A to afford 1.57 g (91%) of ((2R,3S)-3-((tert-butyldiphenylsilyl)oxy)-5-((4-methoxyphenyl)thio)tetrahydrothiophen-2-yl)methyl acetate (Ile) as a clear and colorless oil. $^1$H NMR (400 MHz, chloroform-d) δ 7.65 (m, 4H), 7.51-7.29 (m, 7H), 6.88-6.77 (m, 2H), 4.84 (m, 0.3H), 4.52 (m, 0.7H), 4.39 (m, 0.3H), 4.18 (m, 0.7H), 4.00 (m, 0.7H), 3.83-3.72 (m, 4H), 3.70-3.60 (m, 0.7H), 3.44 (m, 0.3H), 2.36-2.12 (m, 2H), 1.83 (m, 3H), 1.05 (m, 9H).

Preparation of (2R,3S)-2-(Hydroxymethyl)-5-((4-methoxyphenyl)thio)tetrahydrothiophen-3-ol (12e)

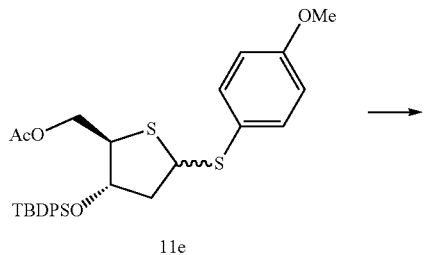

((2R,3S)-3-((tert-Butyldiphenylsilyl)oxy)-5-((4-methoxyphenyl)thio)tetrahydrothiophen-2-yl)methyl acetate (11e) (1.57 g, 2.84 mmol) was reacted with Lithium hydroxide monohydrate (1.192 g, 28.4 mmol) in the manner described in General Method B to afford 0.678 g (88%) of (2R,3S)-2-(hydroxymethyl)-5-((4-methoxyphenyl)thio)tetrahydrothiophen-3-ol (12e) as white solid. $^1$H NMR (400 MHz, chloroform-d) δ 7.51-7.39 (m, 2H), 6.92-6.82 (m, 2H), 4.75-4.67 (m, 1H), 4.51 (m, 0.36H), 4.40 (m, 0.67H), 3.90 (m, 0.34H), 3.80 (m, 3H), 3.73-3.51 (m, 3H), 3.39 (m, 0.34H), 3.18 (m, 0.33H), 2.42-2.16 (m, 3H).

Preparation of (6aR,9aS)-2,2,4,4-tetraIsopropyl-8-((4-methoxyphenyl)thio)tetrahydro-6H-thieno[3,2-f][1,3,5,2,4]trioxadisilocine (13e)

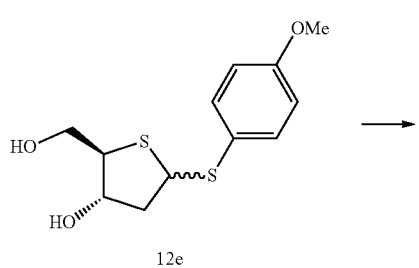

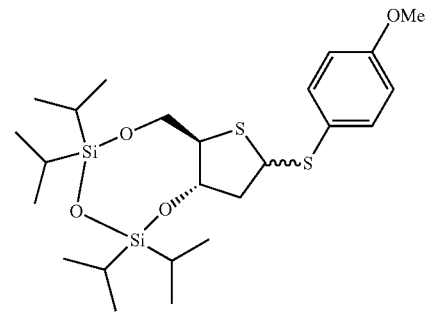

(2R,3S)-2-(hydroxymethyl)-5-((4-methoxyphenyl)thio)tetrahydrothiophen-3-ol (12e) (0.67 g, 2.460 mmol) was reacted with 1,3-dichloro-1,1,3,3-tetraisopropyldisiloxane (0.944 ml, 2.95 mmol) in the manner described in General Method C to afford 1.095 g (86%) of (6aR,9aS)-2,2,4,4-tetraisopropyl-8-((4-methoxyphenyl)thio)tetrahydro-6H-thieno[3,2-f][1,3,5,2,4]trioxadisilocine (13e) as clear and colorless oil. $^1$H NMR (400 MHz, chloroform-d) δ 7.49-7.35 (m, 2H), 6.90-6.79 (m, 2H), 4.66 (m, 0.38H), 4.54 (m, 0.71H), 4.46 (m, 0.39H), 4.23 (m, 0.71H), 4.00 (m, 1H), 3.91-3.73 (m, 4H), 3.30 (m, 1H), 2.57 (0.8H), 2.41-2.26 (m, 0.8H), 2.14-2.00 (m, 0.8H), 1.21-0.87 (m, 28H).

Preparation of ((2R,3S)-3-((tert-Butyldiphenylsilyl)oxy)-5-((4-fluorophenyl)thio)tetrahydrothiophen-2-yl)methyl Acetate (11f)

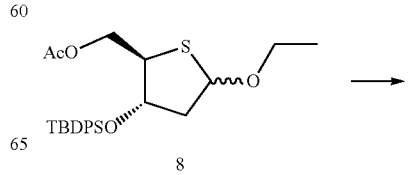

-continued

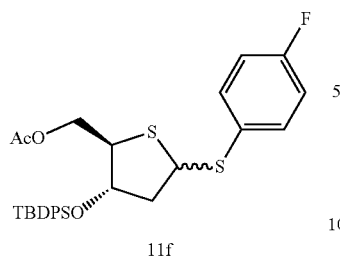

11f ((2S,3R)-3-((tert-Butyldiphenylsilyl)oxy)-5-ethoxytetrahydrothiophen-2-yl)methyl acetate (8) (2 g, 4.36 mmol) was reacted with 4-fluorobenzenethiol (0.511 ml, 4.80 mmol) in the manner described in General Method A to afford 2.28 g (97%) of ((2R,3S)-3-((tert-butyldiphenylsilyl)oxy)-5-((4-fluorophenyl)thio)tetrahydrothiophen-2-yl)methyl acetate 11f as a clear and colorless oil. $^1$H NMR (400 MHz, chloroform-d) δ 7.75-7.57 (m, 4H), 7.49-7.32 (m, 7H), 6.99 (m, 2H), 4.87 (m, 0.22H), 4.60 (m, 0.77H), 4.41 (m, 0.24H), 4.23 (m, 0.8H), 3.97 (m, 0.8H), 3.78 (m, 1H), 3.67 (m, 1H), 3.48 (m, 0.22H), 2.36-2.14 (m, 2H), 1.84 (m 3H), 1.06 (m, 9H).

Preparation of (2R,3S)-5-((4-Fluorophenyl)thio)-2-(hydroxymethyl)tetrahydrothiophen-3-ol (12f)

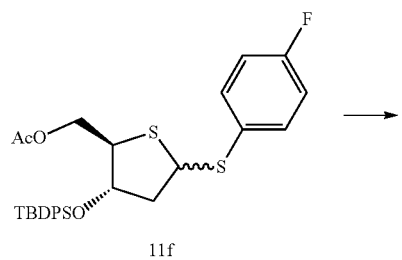

11f

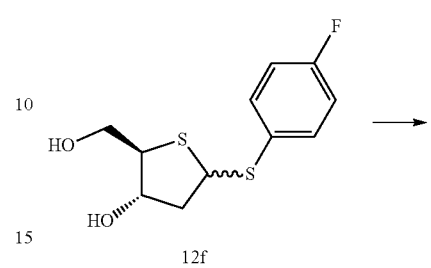

12f ((2R,3S)-3-((tert-butyldiphenylsilyl)oxy)-5-((4-fluorophenyl)thio)tetrahydrothiophen-2-yl)methyl acetate (110 (2.26 g, 4.18 mmol) was reacted with Lithium hydroxide monohydrate (1.754 g, 41.8 mmol) in the manner described in General Method B to afford 1 g (92%) of (2R,3S)-5-((4-fluorophenyl)thio)-2-(hydroxymethyl)tetrahydrothiophen-3-ol (120 as a clear oil.

Preparation of (6aR,9aS)-8-((4-Fluorophenyl)thio)-2,2,4,4-tetraisopropyltetrahydro-6H-thieno[3,2-f][1,3,5,2,4]trioxadisilocine (13f)

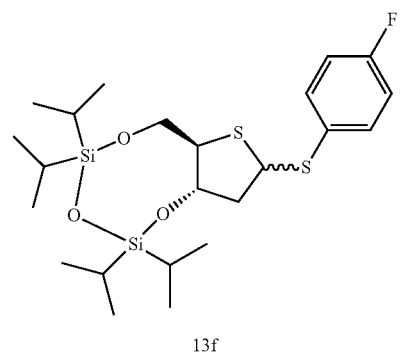

13f (2R,3S)-5-((4-fluorophenyl)thio)-2-(hydroxymethyl)tetrahydrothiophen-3-ol (1.0 g, 3.84 mmol) (12f) was reacted with 1,3-dichloro-1,1,3,3-tetraisopropyldisiloxane (1.475 ml, 4.61 mmol) in the manner described in General Method C to afford 1.67 g (86%) of (6aR,9aS)-8-((4-fluorophenyl)thio)-2,2,4,4-tetraisopropyltetrahydro-6H-thieno[3,2-f][1,3,5,2,4]trioxadisilocine (130 as clear and colorless oil. $^1$H NMR (400 MHz, chloroform-d) δ 7.52-7.37 (m, 2H), 7.01 (m, 2H), 4.67 (m, 0.30H), 4.60 (m, 0.72H), 4.52 (m, 0.30H), 4.25 (m, 0.72H), 4.01 (m, 1H), 3.86 (m, 0.30H), 3.78 (m, 0.70H), 3.32 (m, 1H), 2.60 (m, 0.76H), 2.40-2.30 (m, 0.54H), 2.06 (m, 0.71H), 1.21-0.86 (m, 28H).

Preparation of (6aR,9aS)-2,2,4,4-tetramethyl-8-((4-(octyloxy)benzyl)thio)tetrahydro-6H-thieno[3,2-f][1,3,5,2,4]trioxadisilocine (13g)

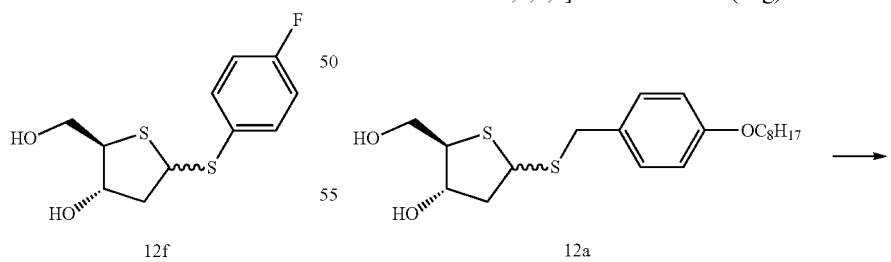

12a

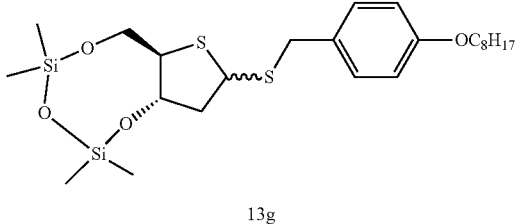

13g (2R,3S)-2-(hydroxymethyl)-5-((4-(octyloxy)benzyl)thio)tetrahydrothiophen-3-ol (3 g, 7.80 mmol) (12a) was reacted with 1,3-dichloro-1,1,3,3-tetramethyldisiloxane (1.831 ml, 9.36 mmol) in the manner described in General Method C to afford 2.07 g (52%) of (6aR,9aS)-2,2,4,4-tetramethyl-8-((4-(octyloxy)benzyl)thio)tetrahydro-6H-thieno[3,2-f][1,3,5,2,4]trioxadisilocine (13g) as clear and colorless oil. $^1$H NMR (400 MHz, chloroform-d) δ 7.18 (dd, J=11.2, 8.4 Hz, 2H), 6.81 (dd, J=8.7, 2.3 Hz, 2H), 4.65 (ddd, J=10.6, 7.2, 5.6 Hz, 1H), 4.24-4.12 (m, 1H), 4.09 (d, J=6.4 Hz, 1H), 4.00-3.83 (m, 4H), 3.77 (dd, J=6.2, 2.8 Hz, 1H), 3.74 (s, 2H), 3.42 (ddd, J=8.9, 7.3, 3.6 Hz, 1H), 2.48-2.33 (m, 1H), 2.26-2.18 (m, 1H), 2.06 (dt, J=12.6, 10.4 Hz, 1H), 1.75 (p, J=6.8 Hz, 2H), 1.43 (p, J=6.9 Hz, 2H), 1.38-1.21 (m, 8H), 0.90-0.83 (m, 3H), 0.22-0.06 (m, 12H).

Preparation of (6aR,9aS)-8-((4-(octyloxy)benzyl)thio)-2,2,4,4-tetraphenyltetrahydro-6H-thieno[3,2-f][1,3,5,2,4]trioxadisilocine (13h)

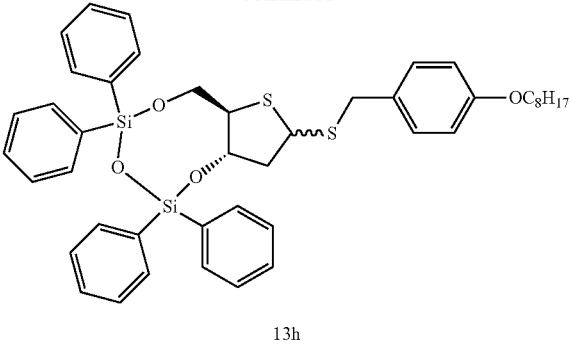

13h (2R,3S)-2-(hydroxymethyl)-5-((4-(octyloxy)benzyl)thio)tetrahydrothiophen-3-ol (3 g, 7.80 mmol) (12a) was reacted with 1,3-dichloro-1,1,3,3-tetraphenyldisiloxane (4.74 ml, 12.48 mmol) in the manner described in General Method C to afford 6.65 g (84%) of (6aR,9aS)-8-((4-(octyloxy)benzyl)thio)-2,2,4,4-tetraphenyltetrahydro-6H-thieno[3,2-f][1,3,5,2,4]trioxadisilocine (13h) as viscous and colorless oil. $^1$H NMR (400 MHz, Chloroform-d) δ 7.79-7.71 (m, 2H), 7.72-7.64 (m, 2H), 7.59-7.50 (m, 4H), 7.46 (dddd, J=11.6, 6.6, 5.6, 2.4 Hz, 3H), 7.43-7.31 (m, 6H), 7.29-7.20 (m, 5H), 7.10-7.01 (m, 2H), 6.81-6.75 (m, 2H), 4.91 (ddd, J=10.3, 7.1, 5.6 Hz, 1H), 4.18-4.07 (m, 2H), 4.03 (dd, J=11.8, 9.0 Hz, 1H), 3.91 (t, J=6.6 Hz, 2H), 3.78-3.66 (m, 2H), 3.65-3.54 (m, 2H), 2.54 (ddd, J=13.0, 10.3, 6.6 Hz, 1H), 2.29 (ddd, J=13.1, 5.6, 1.5 Hz, 1H), 1.81-1.70 (m, 2H), 1.44 (qd, J=8.7, 7.8, 3.7 Hz, 2H), 1.38-1.22 (m, 8H), 0.92-0.82 (m, 3H).

Synthesis of 2'-Deoxynucleosides:

Protected 2'-deoxynucleosides were synthesized as described below. FIG. 6 shows the synthesized compounds.

Example 1. Preparation of 4-amino-1-((6aR,8R,9aS)-2,2,4,4-tetraisopropyltetrahydro-6H-thieno[3,2-f][1,3,5,2,4]trioxadisilocin-8-yl)-1,3,5-triazin-2(1H)-one (15a)

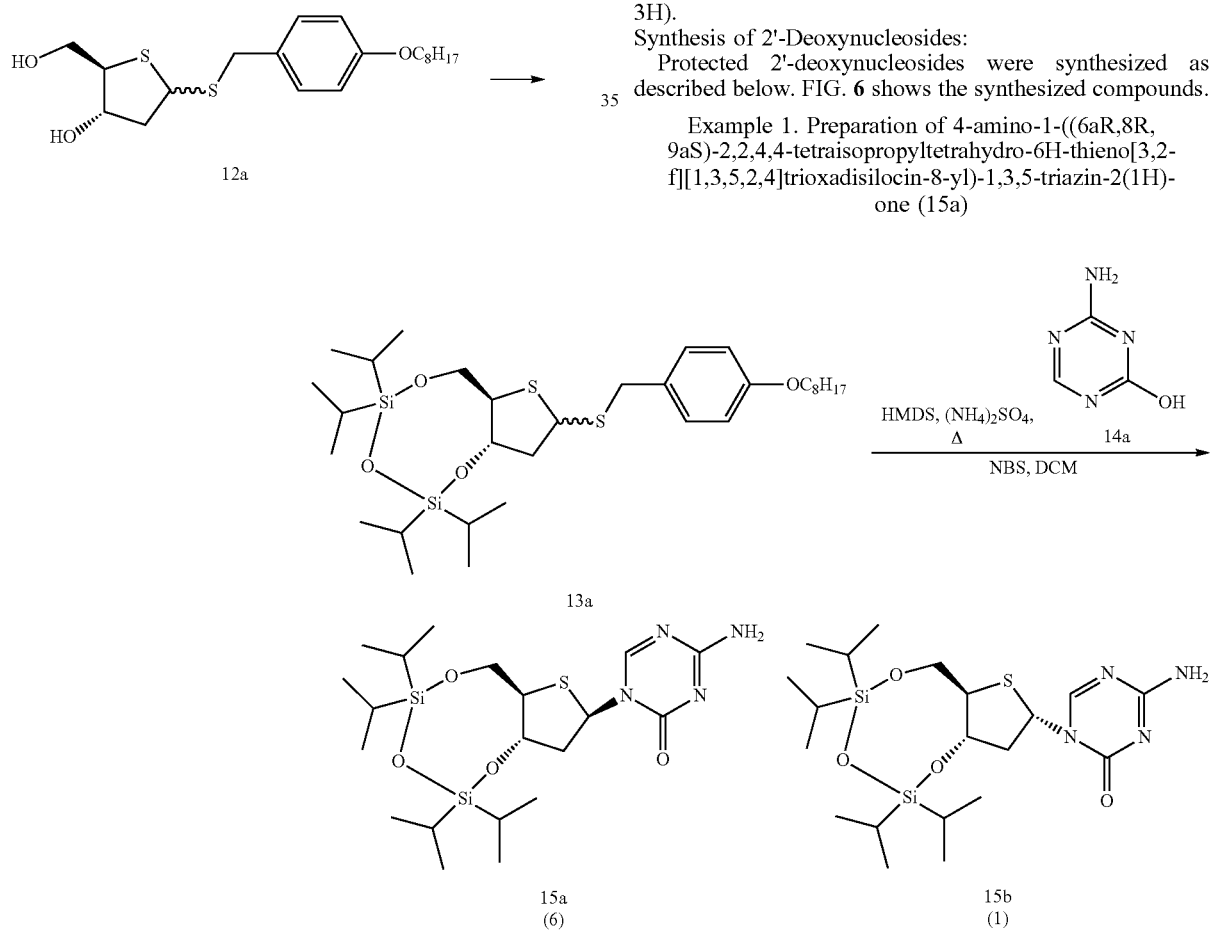

In a 50 mL round bottom flask was added 5-azacytosine (1.947 g, 17.37 mmol) and ammonium sulfate (0.092 g, 0.695 mmol) in HMDS (13.35 ml, 63.7 mmol) and the resulting suspension was heated to 136° C. (reflux) for 18 h. A clear solution was obtained and after cooling to room temperature (rt), the solution was concentrated under reduced pressure (rotoevaporation) until a white solid corresponding to intermediate 14a was isolated.

The residue was redissolved in DCM (30 ml) followed by addition of 3 A molecular sieves (2.5 g, 5.79 mmol) and (6aR,9aS)-2,2,4,4-tetraisopropyl-8-((4-(octyloxy)benzyl)thio)tetrahydro-6H-thieno[3,2-f][1,3,5,2,4]trioxadisilocine (3.63 g, 5.79 mmol) (13a) in DCM (30.0 ml). The suspension was stirred at rt for 10 min and at 0 C for 20 min. NBS (1.133 g, 6.37 mmol) was added in one portion and the resulting orange suspension was stirred at 0 C for 1 h. The reaction was quenched with a solution of $Na_2S_2O_3$ (2.5 g in 30 mL of water) and the mixture was stirred vigorously. After some Celite® diatomaceous earth was added, the suspension was filtered through a plug of Celite® diatomaceous earth and washed with DCM. The aqueous layer was extracted with DCM (2×) and the combined organic layers were dried ($MgSO_4$), filtered and concentrated. An amber foam was recovered.

The residue was then chromatographed on a tandem 50+100 g Biotage® Snap Ultra column eluting on a CombiFlash® system with 0-100 EtOAc/DCM mixture. Two fractions were isolated. The first eluting fraction corresponded to 4-amino-1-46aR,8R,9aS)-2,2,4,4-tetraisopropyltetrahydro-6H-thieno[3,2-f][1,3,5,2,4]trioxadisilocin-8-yl)-1,3,5-triazin-2(1H)-one (1.25 g, 44.4%) (15a) while the second eluting fractions was a 1:1 mixture of 15a:15b (0.48 g, 20.6%). Overall ratio of anomers was ~4:1 in favor of the desired beta anomer (15a). 15a: $^1$H NMR (400 MHz, DMSO-$d_6$) δ 8.55 (s, 1H), 7.57 (d, J=6.1 Hz, 2H), 5.78-5.72 (m, 1H), 4.43 (q, J=8.8 Hz, 1H), 4.03-3.92 (m, 2H), 3.35 (d, J=8.7 Hz, 2H), 2.43 (dd, J=9.8, 5.5 Hz, 2H), 1.09-0.94 (m, 27H). 15a & 15b mix: $^1$H NMR (400 MHz, DMSO-$d_6$) δ 8.62 (s, 1H), 8.52 (s, 2H), 7.54 (d, J=6.3 Hz, 5H), 5.86 (t, J=8.0 Hz, 1H), 5.71 (dd, J=5.8, 3.0 Hz, 2H), 4.40 (q, J=9.0, 8.6 Hz, 2H), 4.28 (td, J=9.5, 6.0 Hz, 1H), 4.03-3.88 (m, 4H), 3.86-3.68 (m, 3H), 3.33 (d, J=6.2 Hz, 2H), 2.45-2.30 (m, 4H), 1.11-0.85 (m, 60H).

Examples 3, 4, 5, 6, 7

Using the procedure exemplified in example 1, thiosugars 13b, 13c, 13d, 13e, 13f were independently reacted with 5-azacytosine to provide a mixture of beta/alpha anomers (ratio determined by examination of crude 1H NMR), with an isolated yield of the beta anomer (when determined) as shown in FIG. 6.

Example 8. Preparation of 4-amino-1-((6aR,8R,9aS)-2,2,4,4-tetramethyltetrahydro-6H-thieno[3,2-f][1,3,5,2,4]trioxadisilocin-8-yl)-1,3,5-triazin-2(1H)-one (15g) and 4-amino-1-((6aR,8s,9aS)-2,2,4,4-tetramethyltetrahydro-6H-thieno[3,2-f][1,3,5,2,4]trioxadisilocin-8-yl)-1,3,5-triazin-2(1H)-one (15H)

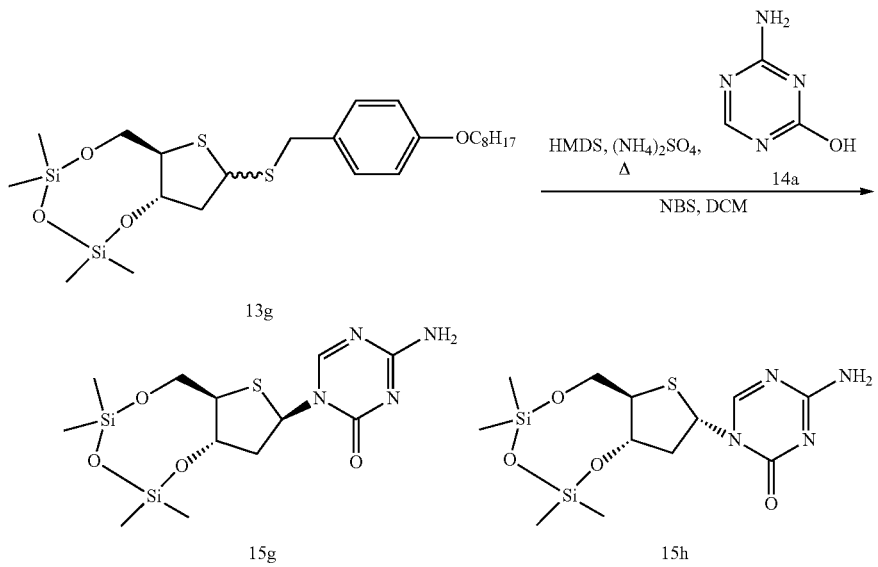

(6aR,9aS)-2,2,4,4-tetramethyl-8-((4-(octyloxy)benzyl)thio)tetrahydro-6H-thieno[3,2-f][1,3,5,2,4]trioxadisilocine (0.86 g, 1.670 mmol) (13g) was reacted with 5-azacytosine (0.562 g, 5.01 mmol) in the manner described in General Method D to afford 4-amino-1-((6aR,8R,9aS)-2,2,4,4-tetramethyltetrahydro-6H-thieno[3,2-f][1,3,5,2,4]trioxadisilocin-8-yl)-1,3,5-triazin-2(1H)-one (15g) and 4-amino-1-((6aR,8s,9aS)-2,2,4,4-tetramethyltetrahydro-6H-thieno[3,2-f][1,3,5,2,4]trioxadisilocin-8-yl)-1,3,5-triazin-2(1H)-one (15h) as a 2.5:1 mixture of anomers (β:α) as determined by crude $^1$H NMR. LCMS for $C_{12}H_{23}N_4O_4SSi_2[M+H]^+$ calculated: 375.10. found: 375.6.

Example 9. Preparation of 4-amino-1-((6aR,8R, 9aS)-2,2,4,4-tetraphenyltetrahydro-6H-thieno[3,2-f] [1,3,5,2,4]trioxadisilocin-8-yl)-1,3,5-triazin-2(1H)-one (15i) and 4-amino-1-((6aR,8S,9aS)-2,2,4,4-tetraphenyltetrahydro-6H-thieno[3,2-f][1,3,5,2,4] trioxadisilocin-8-yl)-1,3,5-triazin-2(1H)-one (15j)

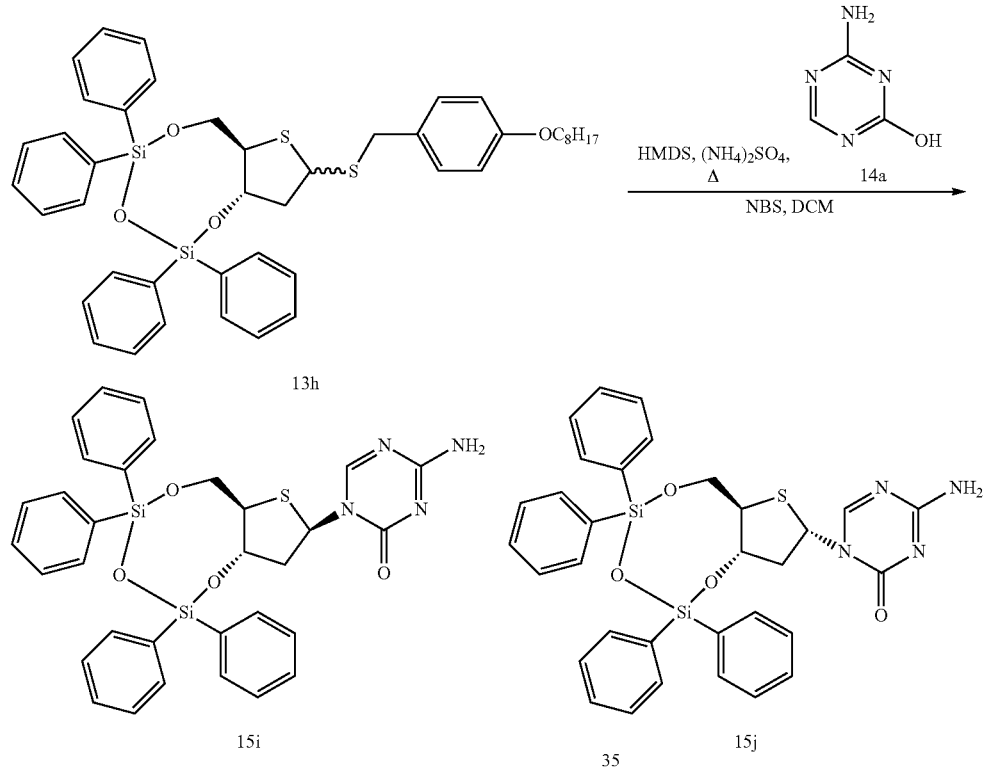

(6aR,9aS)-8-((4-(octyloxy)benzyl)thio)-2,2,4,4-tetraphenyltetrahydro-6H-thieno[3,2-f][1,3,5,2,4]trioxadisilocine (2 g, 2.62 mmol) (13h) was reacted with 5-azacytosine (0.881 g, 7.86 mmol) in the manner described in the General Method D to afford 0.64 g (40%) of 4-amino-1-((6aR,8R, 9aS)-2,2,4,4-tetraphenyltetrahydro-6H-thieno[3,2-f][1,3,5, 2,4]trioxadisilocin-8-yl)-1,3,5-triazin-2(1H)-one (15i) and 4-amino-1-((6aR,8S,9aS)-2,2,4,4-tetraphenyltetrahydro-6H-thieno[3,2-f][1,3,5,2,4]trioxadisilocin-8-yl)-1,3,5-triazin-2(1H)-one (15j) as a 4:1 mixture of anomers (β:α) as determined by crude $^1$H NMR. $^1$H NMR (400 MHz, DMSO-$d_6$) δ 11.96 (s, 2H), 8.64 (s, 1H), 8.12 (s, 4H), 7.69 (d, J=6.5 Hz, 7H), 7.66-7.61 (m, 8H), 7.56-7.37 (m, 63H), 7.33 (dd, J=7.6, 4.0 Hz, 19H), 4.82-4.74 (m, 5H), 4.49 (q, J=8.3 Hz, 1H), 4.12 (d, J=5.2 Hz, 9H), 3.95 (dd, J=12.1, 5.7 Hz, 1H), 3.68 (dt, J=8.0, 5.1 Hz, 5H), 2.71-2.60 (m, 5H), 2.54 (d, J=6.2 Hz, 3H).

Examples 2 and 10

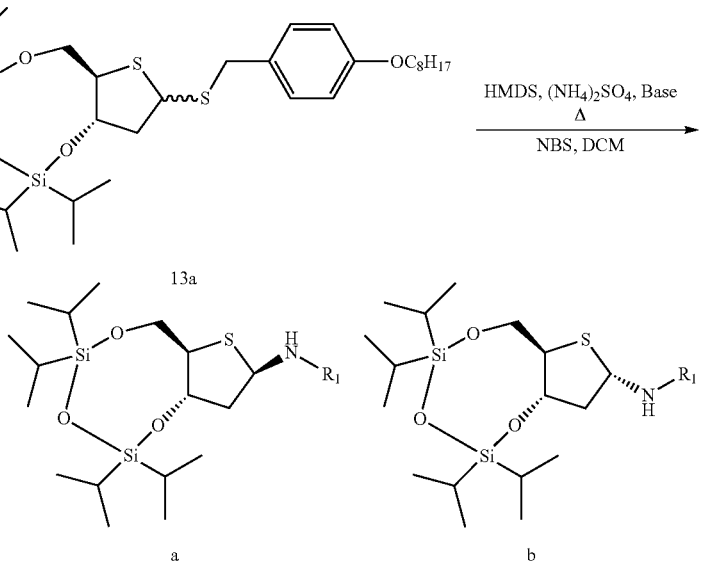

The nucleosides in examples 2 and 10 were prepared in the manner described in Example 1, reacting (6aR,9aS)-2,2,4,4-tetraisopropyl-8-((4-(octyloxy)benzyl)thio)tetrahydro-6H-thieno[3,2-f][1,3,5,2,4]trioxadisilocine (13a) with the appropriate base. The results are shown in Table 2.

TABLE 2

| Base (R₁) | Example | Yield | Ratio (β:α) |
|---|---|---|---|
| NH₂ / pyrimidine with F (5-F-cytosine) | 10 | Not determined | 4:1 (determined by crude ¹H NMR) |
| Bz-NH / pyrimidine (N4-Bz-cytosine) | 2 | 65% | 5.2:1 (determined by crude ¹H NMR) |

Example 10: LCMS for $C_{21}H_{38}FN_3O_4SSi_2$ [M]⁺ calculated: 503.23. found: 503.1. Example 2: ¹H NMR (400 MHz, DMSO-$d_6$) δ 11.31 (s, 1H), 11.13-11.01 (m, 1H), 8.51 (d, J=7.5 Hz, 1H), 8.01 (d, J=7.7 Hz, 2H), 7.63 (t, J=7.4 Hz, 1H), 7.52 (t, J=7.6 Hz, 2H), 7.40 (d, J=7.4 Hz, 1H), 5.91 (d, J=7.0 Hz, 1H), 4.44-4.35 (m, 1H), 4.07-3.95 (m, 2H), 3.40 (d, J=8.8 Hz, 1H), 2.56 (s, 3H), 2.38 (dd, J=13.4, 5.6 Hz, 1H), 1.14-0.88 (m, 23H).

Large-Scale Synthesis of 5-Aza-T-Cyd from Diol Intermediate

Materials:

Diol compound 12a (98%) could be prepared as outlined in General Method B; 1,3-dichloro-1,1,3,3,tetra-isopropyl-disiloxane and imidazole were obtained from Oakwood Chemicals; aza-cytosine (95%+) was obtained from Matrix Scientific; hexamethyldisilazane (99.9%, HMDS), N-bromosuccinimide (98%, NBS), methanol, NH₄F (98%), and diethyl ether were obtained from Sigma-Aldrich; molecular sieves were obtained from Alfa-Aesar; dimethylformamide, dichloromethane and (NH₄)₂SO₄ were obtained from Acros Organics.

The overall scheme for synthesis of 5-aza-T-dCyd is shown in FIG. 7.

S-(4-octyloxy)benzyl-2-deoxy-3,5-O-[1,1,3,3-tetrakis(1-methylethyl)-1,3-disiloxanediyl]-1,4-dithio-erythro-pentofuranoside (6aR,9aS)-2,2,4,4-Tetraisopropyl-8-((4-(octyloxy)benzyl)thio)tetrahydro-6H-thieno[3,2-f][1,3,5,2,4]trioxadisilocine (13a)

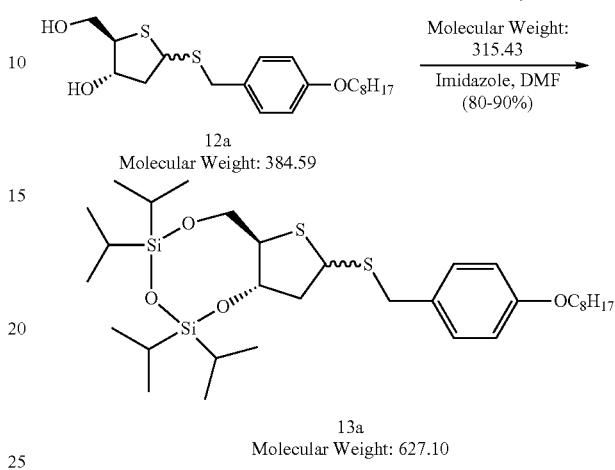

12a
Molecular Weight: 384.59

13a
Molecular Weight: 627.10

To a solution of (2R,3S)-2-(hydroxymethyl)-5-((4-(octyloxy)benzyl)thio)tetrahydrothiophen-3-ol (12a) (187 g, 486.2 mmol) and imidazole (82.7 g, 1215.5 mmol, 2.5 equiv.) in anhydrous DMF (935 mL) under argon at 0° C., 1,3-dichloro-1,1,3,3-tetraisopropyldisiloxane (184.0 g, 583.4 mmol, 1.2 equiv.) was added while keeping the temperature of the reaction mixture below 5° C. The reaction mixture was stirred for 21 hours, during which period the reaction temperature was allowed to rise from at 5° C. to ambient. The mixture was poured into ice cold water (2 L) and the product was extracted with ethyl acetate (4 L). The organic layer was separated and washed with 50% brine (1 L×3). The organic layer was dried over anhydrous Na₂SO₄ (100 g) for 20 h and ethyl acetate was removed in a rotary evaporator to provide a residue 380 g. The crude product was purified by chromatography on silica gel (3800 g) eluted with heptanes/ethyl acetate in a ratio 97:3 (30 L) to give the target product (13a) as a colorless oil (280 g, yield 89.2%). Purity estimated at ~95% based on ¹H NMR spectrum.

4-Amino-1-((6aR,8R,9aS)-2,2,4,4-tetraisopropyltetrahydro-6H-thieno[3,2-f][1,3,5,2,4]trioxadisilocin-8-yl)-1,3,5-triazin-2(1H)-one (15a)

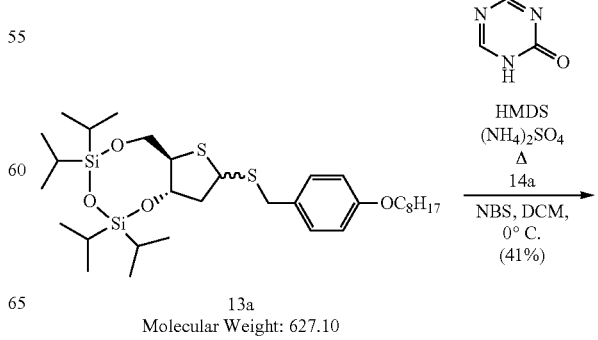

13a
Molecular Weight: 627.10

-continued

15a
Molecular Weight: 486.78

A suspension of 5-azacytosine (14a) (150.1 g, 1.339 mol) and ammonium sulfate (4.4 g, 33.3 mmol) in hexamethyldisilazane (HMDS, 980 mL) was refluxed in 2-L round-bottomed flask at stirring under argon atmosphere for 21 h. The solution was cooled to ambient temperature and excess of HMDS was removed in a rotary evaporator to give a white solid. The residue was dissolved in anhydrous dichloromethane (1 L) and the solution was used in the step below.

(6aR,9aS)-2,2,4,4-Tetraisopropyl-8-((4-(octyloxy)benzyl)thio)tetrahydro-6H-thieno[3,2-f][1,3,5,2,4]trioxadisilocine (13a) (280 g, 446.5 mmol) was dissolved in anhydrous dichloromethane (1300 mL) and the solution of the silylated azacytosine was added. The resulting solution was cooled to 0° C. while stirring under argon atmosphere. N-Bromosuccinimide (87 g, 491.1 mmol, 1.1 equiv.) was added to the cooled mixture in 5 portions over 30 minutes. The resulting mixture was stirred at 0° C. for 1.5 h. Thin-layer chromatography was used to monitor consumption of starting material 3 (heptanes:ethyl acetate=19:1). After 13a was consumed completely, the reaction mixture was quenched with sodium thiosulfate (160 g in 1800 mL of water) and stirred for 0.5 h at 0° C. The mixture was filtered through a pad of Celite 209 (200 g). The organic layer was separated and the aqueous layer was extracted with dichloromethane (1.5 L×2). The combined organic layers were dried over sodium sulfate (200 g) for 14 h, clarified by filtration and concentrated in a 10-L rotary evaporator to give a crude product (420 g).

Isolation of Intermediate 15a from a Mixture of Anomers by Chromatography:

The crude product from the above step was purified by column chromatography on silica gel (kg). The product was eluted with a gradient of ethyl acetate in dichloromethane 30% to 100% to give four fractions:

F1: 9 g (15a contaminated with less polar impurities);
F2: 29.0 g (pure β anomer);
F3: 56 g (α and 88% β mixture);
F4: 35 g (α and 68% β mixture).

Fraction 3 was eluted through a column of silica gel (1200 g) with heptanes:ethyl acetate:triethyl amine (1:1:1%, 36 L) to give 38 g of pure product 15a.

Fraction 4 was eluted through a column of silica gel (1200 g) with heptanes:ethyl acetate:triethyl amine (1:1:1%, 33 L) to give 23.8 g of pure product 15a.

The total isolated amount of 15a was 90.6 grams (yield 41.7%).

4-Amino-1-(2-deoxy-4-thio-(3-erythro-pentofuranosyl)-1,3,5-triazin-2(1H)-one (5-Aza-T-dCyd)

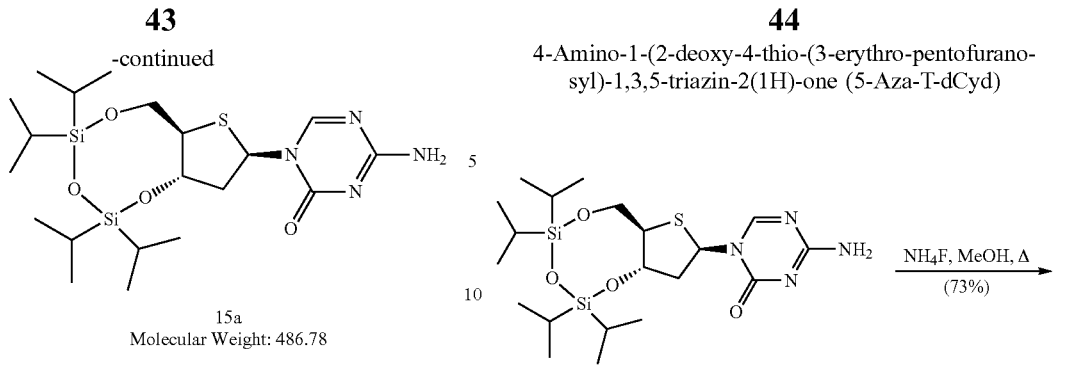

15a
Molecular Weight: 486.78

Molecular Weight: 244.27

A suspension of 4-amino-1-(6aR,8R,9aS)-2,2,4,4-tetraisopropyl-tetrahydro-6H-thieno[3,2-f][1,3,5,2,4]trioxadisilocin-8-yl)-1,3,5-triazin-2(1H)-one (15a) 90 g, 184.9 mmol) and ammonium fluoride (34.3 g, 924.4 mmol) in anhydrous methanol (1304 mL) was heated to 60-65° C. for 2.5 h. The mixture was cooled to 15° C. and stirred for 1 h. A precipitated solid was collected in a filter funnel and washed with anhydrous methanol (2×30 mL) to give 4-amino-1-(2-deoxy-4-thio-(3-erythro-pentofuranosyl)-1,3, 5-triazin-2(1H)-one (5-Aza-T-dCyd) as white solid (after drying 28 g, 100% pure as per HPLC). The mother liquor was mixed with Celite 209 (30 g), concentrated to dryness and purified by chromatography on silica gel (150 g) eluted with ethyl acetate:ethanol in a ratio 5:3 (4 L) and then with ethanol (4 L) to give 7 g of crude product, which was stirred with methanol (70 mL) for 30 min., followed by filtration to provide additional 3.5 g of product as white solid after drying (99.3% pure by HPLC). Two portion of the product (5) were mixed and released (HPLC: 99.3%; 31.5 g, yield: 72.9%).

The product, 2'-deoxy-4'-thio-5-aza-cytidine, a white powder, was characterized by $^1$H, $^{13}$C NMR spectroscopy, elemental analyses for C, H, N and F, and HPLC (area % at 225 nm). The results of analyses conformed to the structure of 5-aza-T-dCyd and proved to be HPLC-identical to an NCI-provided sample of the product. The overall yield of the synthesis was 21-22%, as compared to 14.6% obtained by a prior method requiring supercritical fluid chromatography.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:
1. A method for stereoselective synthesis of a β-anomer of a nucleoside, the method comprising:
providing a compound having a structure and stereochemistry according to Formula I

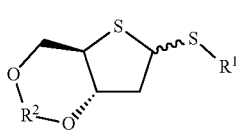
(I)

wherein R¹ is optionally substituted —(CH₂)ₙ-aryl, or —(CH₂)ₙ-alkyl where n is 0, 1, or 2; and R² is a protecting group having a formula —Si(Rᵃ)(Rᵇ)—O—Si(Rᵃ)(Rᵇ)— where each Rᵃ and Rᵇ independently is alkyl, cycloalkyl, or aryl;

combining the compound according to Formula I with N-bromosuccinimide and a silylated pyrimidine or triazine under reaction conditions effective to produce a mixture of α- and β-anomers of a protected nucleoside, wherein the mixture of α- and β-anomers has a β/α mass ratio of at least 2:1;

separating the β-anomer from the α-anomer of the protected nucleoside; and removing the protecting group from the β-anomer of the protected nucleoside to provide a β-anomer of a nucleoside.

2. The method of claim 1, wherein Rᵃ and Rᵇ independently are C₁-C₄ alkyl, cycloalkyl, or phenyl.

3. The method of claim 1, wherein Rᵃ and Rᵇ are the same.

4. The method of claim 1, wherein R² is —Si(CH(CH₃)₂)₂—O—Si(CH(CH₃)₂)₂—, —Si(CH₃)₂—O—Si(CH₃)₂—, or —Si(C₆H₅)₂—O—Si(C₆H₅)₂—.

5. The method of claim 1, wherein R¹ is aryl or —(CH₂)ₙ-aryl, the aryl is optionally substituted with alkyl, alkoxy, or halo, and n=0 or 1.

6. The method of claim 1, wherein R¹ is:

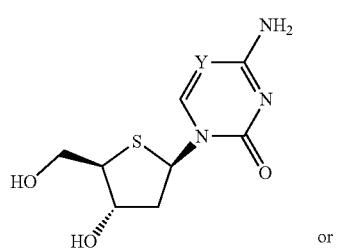

7. The method of claim 1, wherein the β-anomer of the nucleoside has a general structure:

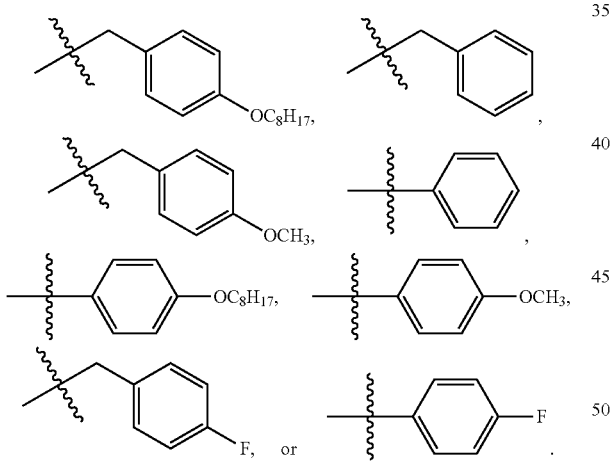

or wherein Y is N, C(H), C(CH₃) or C(X) where X is halo.

8. The method of claim 7, wherein the β-anomer of the nucleoside has a general structure:

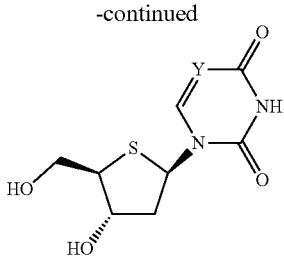

9. The method of claim 8, wherein the β-anomer of the nucleoside is

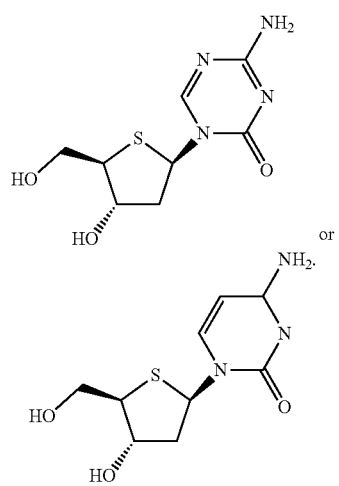

10. The method of claim 1, wherein the compound according to Formula I is combined with a molar excess of N-bromosuccinimide.

11. The method of claim 1, wherein the compound according to Formula I is combined with a molar excess of the silylated pyrimidine or triazine.

12. The method of claim 1, wherein reaction conditions effective to produce a mixture of α- and β-anomers of a protected nucleoside comprise (i) a reaction temperature within a range of from −10 to 10° C., (ii) a reaction time within a range of from 30 minutes to 3 hours, or (iii) both (i) and (ii).

13. The method of claim 1, wherein separating the β-anomer from the α-anomer of the protected nucleoside comprises silica gel chromatography.

* * * * *